US012421525B2

(12) United States Patent
Byrne et al.

(10) Patent No.: US 12,421,525 B2
(45) Date of Patent: Sep. 23, 2025

(54) CONJUGATES COMPRISING AAVS AND CAS9 POLYPEPTIDES

(71) Applicants: University of Pittsburgh—Of the Commonwealth System of Higher Education, Pittsburgh, PA (US); The Regents of the University of California, Oakland, CA (US)

(72) Inventors: Leah Byrne, Pittsburgh, PA (US); Bilge Esin Ozturk, Pittsburgh, PA (US); Timothy Day, Berkeley, CA (US)

(73) Assignees: University of Pittsburgh—of the Commonwealth System of Higher Education, Pittsburgh, PA (US); The Regents of the University of California, Oakland, CA (US)

( * ) Notice: Subject to any disclaimer, the term of this patent is extended or adjusted under 35 U.S.C. 154(b) by 1108 days.

(21) Appl. No.: 16/976,720

(22) PCT Filed: Feb. 28, 2019

(86) PCT No.: PCT/US2019/020096
§ 371 (c)(1),
(2) Date: Aug. 28, 2020

(87) PCT Pub. No.: WO2019/169159
PCT Pub. Date: Sep. 6, 2019

(65) Prior Publication Data
US 2020/0407751 A1 Dec. 31, 2020

Related U.S. Application Data

(60) Provisional application No. 62/636,638, filed on Feb. 28, 2018.

(51) Int. Cl.
| | | |
|---|---|---|
| *A01N 63/00* | (2020.01) | |
| *A61K 48/00* | (2006.01) | |
| *C12N 7/00* | (2006.01) | |
| *C12N 9/22* | (2006.01) | |
| *C12N 15/11* | (2006.01) | |
| *C12N 15/86* | (2006.01) | |

(52) U.S. Cl.
CPC .............. *C12N 15/86* (2013.01); *A61K 48/00* (2013.01); *C12N 7/00* (2013.01); *C12N 9/22* (2013.01); *C12N 15/11* (2013.01); *C12N 2310/20* (2017.05); *C12N 2750/14121* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2014/0256802 A1 | 9/2014 | Boye et al. |
| 2015/0126588 A1 | 5/2015 | Nakai et al. |
| 2016/0102322 A1 | 4/2016 | Ravinder et al. |
| 2018/0155708 A1 | 6/2018 | Church et al. |
| 2018/0282720 A1 | 10/2018 | Winslow et al. |
| 2022/0073905 A1 | 3/2022 | Byrne et al. |
| 2022/0348613 A1 | 11/2022 | Byrne et al. |
| 2024/0124892 A1 | 4/2024 | Byrne et al. |

FOREIGN PATENT DOCUMENTS

| | | |
|---|---|---|
| JP | 2009-519710 A | 5/2009 |
| JP | 2012-519008 | 8/2012 |
| JP | 2017-532024 A | 11/2017 |
| WO | WO 2014/194132 | 12/2014 |
| WO | WO 2016/112921 | 7/2016 |
| WO | WO 2016/131009 | 8/2016 |
| WO | WO 2016/134375 | 8/2016 |
| WO | WO 2017/164936 | 9/2017 |
| WO | WO 2017/197238 | 11/2017 |
| WO | WO 2017/197355 | 11/2017 |
| WO | WO 2018/035503 | 2/2018 |
| WO | WO 2018/071831 | 4/2018 |
| WO | WO 2019/006046 | 1/2019 |
| WO | WO 2019/084015 A1 | 5/2019 |
| WO | WO 2019/169159 | 9/2019 |
| WO | WO 2020/242984 | 12/2020 |
| WO | WO 2022/187377 | 9/2022 |

OTHER PUBLICATIONS

Zakeri (PNAS, 2012, vol. 109, E690-697).*
Veggiani (PNAS, 2016, vol. 113, p. 1202-1207).*
Keeble (Chem Int Ed Engl. 2017, vol. 56, p. 16521-16525).*
Kim (Biomaterials, 2011, vol. 32, p. 8654-8662).*
Gomez (ACS nano, 2016, vol. 10, No. 1, p. 225-237).*
Koerber (Human Gene Therapy, 2007, vol. 18, p. 367-378).*
Brune (Scientific Reports, 2016, vol. 6, Article 19234, p. 1-13).*
Roder (Small, 2017, vol. 13, No. 48, p. 1-12).*
Kasaraneni (mBio, 2017, vol. 8, No. 6, p. 1-12).*
UniProt Accession No. A0A221C9L1_STREQ, "Fibronectin binding protein B." dated Oct. 25, 2017, 6 pages.

(Continued)

*Primary Examiner* — Michael C Wilson
(74) *Attorney, Agent, or Firm* — Fish & Richardson P.C.

(57) ABSTRACT

In one embodiment, the invention provides an Adeno-Associated Virus (AAV) comprising an exterior surface, which surface comprises one or more peptide tags that form a bond with a binding-partner, wherein the AAV is a live virus. In another embodiment, the invention provides a conjugate comprising at least one such AAV and at least one polypeptide comprising a first domain which is the binding-partner for the tag and a second domain, which is a bioactive polypeptide. In another embodiment, the invention provides a conjugate comprising at least one such AAV (first AAV) and at least one second AAV, which second AAV comprises a second exterior surface, which second exterior surface comprises at least one binding-partner for the tag or for a third linker molecule, wherein the at least one first AAV and the at least one second AAV are bound.

7 Claims, 4 Drawing Sheets

Figure 1:
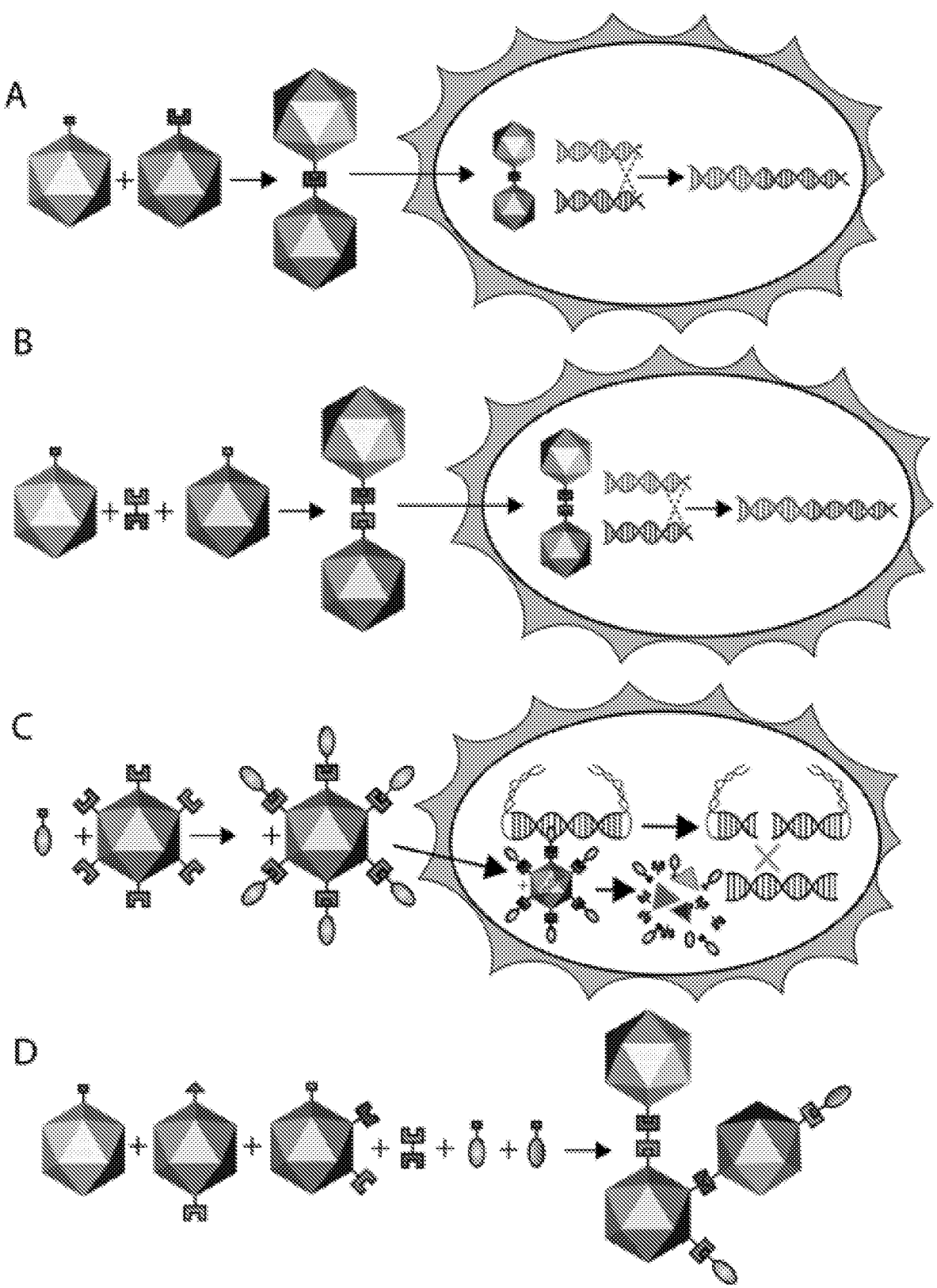

Specification includes a Sequence Listing.

(56) References Cited

OTHER PUBLICATIONS

Fierer et al., "SpyLigase peptide-peptide ligation polymerizes affibodies to enhance magnetic cancer cell capture," Proceedings of the National Academy of Sciences, Mar. 2014, 111(13):E1176-E1181.
Davidsson et al., "542. Novel Barcode-Based In Vivo Screening Method for Generating De Novo AAV Serotypes for CNS-Directed Gene Therapy," Mol. Therapy, May 2016, 24(S1): S216-S217.
EP Extended Search Report in European Appln. No. 19902231.0, dated Feb. 9, 2022, 13 pages.
Xu et al., "Integrated measurement of intracellular proteins and transcripts in single cells," Lab Chip, Aug. 27, 2018, 18(21):3251-3262.
Aurnhammer et al., "Universal real-time PCR for the detection and quantification of adeno-associated virus serotype 2-derived inverted terminal repeat sequences," Human Gene Therapy, Part. B: Methods, Feb. 2012, 23(1):18-28.
Brune et al., "Plug-and-Display: decoration of Virus-Like Particles via isopeptide bonds for modular immunization," Scientific Reports, Jan. 2016, 6:19234.
Byrne et al., "Viral-mediated RdCVF and RdCVFL expression protects cone and rod photoreceptors in retinal degeneration," The Journal of Clinical Investigation, Jan. 2015, 125(1):105-16.
Duan et al., "Expanding AAV packaging capacity with trans-splicing or overlapping vectors: a quantitative comparison," Molecular Therapy, Oct. 2001, 4(4):383-91.
Feinberg et al., "GFP Reconstitution Across Synaptic Partners (GRASP) defines cell contacts and synapses in living nervous systems," Neuron, Feb. 2008, 57(3):353-63.
Grieger et al., "Production and characterization of adeno-associated viral vectors," Nature Protocols, Aug. 2006, 1(3):1412-28.
Keeble et al., "Evolving accelerated amidation by SpyTag/SpyCatcher to analyze membrane dynamics," Angewandte Chemie International Edition, Dec. 2017, 56(52):16521-5.
Kobashigawa et al., "Attachment of an NMR-invisible solubility enhancement tag using a sortase-mediated protein ligation method," Journal of Biomolecular NMR, Mar. 2009, 43(3):145.
Maddalena et al., "Triple vectors expand AAV transfer capacity in the retina," Molecular Therapy, Feb. 2018, 26(2):524-41.
PCT International Preliminary Report on Patentability in International Appln. No. PCT/US2019/020072, dated Sep. 1, 2020, 7 pages.
PCT International Preliminary Report on Patentability in International Appln. No. PCT/US2019/020096, dated Sep. 1, 2020, 5 pages.
PCT International Search Report and Written Opinion in International Appln. No. PCT/US2019/020072, dated Jun. 7, 2019, 11 pages.
PCT International Search Report and Written Opinion in International Appln. No. PCT/US2019/020096, dated May 8, 2019, 8 pages.
Tan et al., "Kinetic controlled Tag-Catcher interactions for directed covalent protein assembly," PLoS One, Oct. 2016, 11(10):e0165074.
Thrane et al., "Bacterial superglue enables easy development of efficient virus-like particle based vaccines," Journal of Nanobiotechnology, Dec. 2016, 14(1):1-6.
Truong et al., "Development of an intein-mediated split-Cas9 system for gene therapy," Nucleic Acids Research, Jul. 2015, 43(13):6450-8.
Veggiani et al., "Programmable polyproteams built using twin peptide superglues," Proceedings of the National Academy of Sciences, Feb. 2016, 113(5):1202-7.
Wu et al., "Protein trans-splicing by a split intein encoded in a split DnaE gene of *Synechocystis* sp. PCC6803," Proceedings of the National Academy of Sciences, Aug. 1998, 95(16):9226-31.
Yao et al., "Caspase inhibition with XIAP as an adjunct to AAV vector gene-replacement therapy: improving efficacy and prolonging the treatment window," PLoS One, May 2012, 7(5):e37197.
Zakeri et al., "Peptide tag forming a rapid covalent bond to a protein, through engineering a bacterial adhesin," Proceedings of the National Academy of Sciences, Mar. 2012, 109(12):E690-7.
JP Office Action in Japanese Appln. No. 2020-545308, dated Feb. 20, 2024, 9 pages (with English translation).
Kotterman et al., "Engineering adeno-associated viruses for clinical gene therapy," Nat. Rev. Genet., Jul. 2014, 15(7):445-451.
Haque et al., "A practical guide to single-cell RNA-sequencing for biomedical research and clinical applications," Genome Med., Aug. 2017, 9:75, 12 pages.
Ishigaki et al., "MHC-identical and transgenic cynomolgus macaques for preclinical studies," Inflamm. Regen., Nov. 2018, 38:30, 6 pages.
NIH.gov [online], "NIH Will No Longer Support Biomedical Research on Chimpanzees," Nov. 17, 2015, retrieved on Feb. 19, 2025, retrieved from URL<https://www.nih.gov/about-nih/who-we-are/nih-director/statements/nih-will-no-longer-support-biomedical-research-chimpanzees>, 2 pages.
U.S. Appl. No. 17/638,451, filed Feb. 25, 2022, Leah Byrne, Pending.
U.S. Appl. No. 17/416,601, filed Jun. 17, 2021, Leah Byrne, Pending.
Ponnazhagan et al., "Conjugate-Based Targeting of Recombinant Adeno-Associated Virus Type 2 Vectors by Using Avidin-Linked Ligands," J. Virology, Dec. 2002, 76(24):12900-12907.
Adachi et al., "Drawing a high-resolution functional map of adeno-associated virus capsid by massively parallel sequencing," Nat. Communications, Jan. 17, 2014, 5:3075, 14 pages.
Adachi et al., "Simultaneous Pharmacokinetic Profiling of Multiple AAV Serotypes and Mutants in a Non-Human Primate by AAV Barcode-Seq," Mol. Ther. AAV Vector Biology, May 1, 2013, 21(SI):S31-S32.
Chan et al., "Engineered AAVs for efficient noninvasive gene delivery to the central and peripheral nervous systems," Nat. Neuroscience, Jun. 26, 2017, 20(8): 1172-1179.
Davidsson et al., "Barcoded Rational AAV Vector Evolution enables systematic in vivo mapping of peptide binding motifs," bioRxiv, May 31, 2018, 335372, 59 pages.
Marsic et al., "High-accuracy biodistribution analysis of adeno-associated virus variants by double barcode sequencing," Mol. Ther. Methods Clin. Development, Oct. 28, 2015, 2:15041, 7 pages.
Shen et al., "Massively parallel cis-regulatory analysis in the mammalian central nervous system," Genome Research, Feb. 2016, 26(2):238-255.
Boucas et al., "Engineering adeno-associated virus serotype 2-based targeting vectors using a new insertion site-position 453-and single point mutations," J. Gene Med., Dec. 2009, 11(12):1103-1113.
Buning et al., "Engineering the AAV capsid to optimize vector-host-interactions," Curr. Opin. Pharmacol., Oct. 2015, 24:94-104.
Lee et al., "Adeno-Associated Virus (AAV) Vectors: Rational Design Strategies for Capsid Engineering," Curr. Opin. Biomed. Eng., Sep. 2018, 7:58-63.

* cited by examiner

SEQUENCE LISTING

<160> NUMBER OF SEQ ID NOS: 14

<210> SEQ ID NO 1
<211> LENGTH: 2261
<212> TYPE: DNA
<213> ORGANISM: Artificial Sequence
<220> FEATURE:
<223> OTHER INFORMATION: Synthetic

<400> SEQUENCE: 1

```
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg acccttcaa cggactcgac      180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt ggggcaacc tcggacgagc agtcttccag      360
gcgaaaaaga gggttcttga acctctgggc ctggttgagg aacctgttaa dacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg acccccagcc tctcggacag ccaccagcag cccctctgg tctgggaact      600
aatacgatgg ctacaggcag tggcgcacca atggcagaca taacgaggg cgccgacgga      660
gtgggtaatt cctcgggaaa ttggcattgc gattccacat ggatgggcga cagagtcatc     720
accaccagca cccgaacctg ggccctgccc acctacaaca accacctcta caaacaaatt     780
tccagccaat caggagcctc gaacgacaat cactactttg ctacagcac ccttgggg      840
tattttgact tcaacagatt ccactgccac ttttcaccac gtgactggca aagactcatc     900
aacaacaact ggggattccg acccaagaga ctcaacttca gctctttaa cattcaagtc      960
aaagaggtca cgcagaatga cggtacgacg acgattgcca ataaccttac cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcacccctg   1140
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa caccggtgcc cacatcgtga tggtggacgc ctacaagccg    1800
acgaagggct taagtagaca agcagctacc gcagatgtca acacacaagg cgttcttcca    1860
ggcatggtct ggcaggacag agatgtgtac cttcagggc ccatctgggc aaagattcca    1920
cacacggacg gacattttca cccctctccc ctcatgggtg gattcggact aaacaccct    1980
cctccacaga ttctcatcaa gaacacccg gtacctgcga atccttcgac caccttcagt    2040
```

| | |
|---|---|
| gcggcaaagt tgcttcctt catcacacag tactccacgg gacaggtcag cgtggagatc | 2100 |
| gagtgggagc tgcagaagga aaacagcaaa cgctggaatc ccgaaattca gtacacttcc | 2160 |
| aactacaaca gtctgttaa tgtggacttt actgtggaca ctaatggcgt gtattcagag | 2220 |
| cctcgcccca ttggcaccag atacctgact cgtaatctgt a | 2261 |

```
<210> SEQ ID NO 2
<211> LENGTH: 2258
<212> TYPE: DNA
<213> ORGANISM: Artificial Sequence
<220> FEATURE:
<223> OTHER INFORMATION: Synthetic

<400> SEQUENCE: 2
```

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg tcttgtgct tcctgggtac aagtacctcg gacccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt gggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg accccagcc tctcggacag ccaccagcag cccctctgg tctgggaact | 600 |
| aatacgatgg ctacaggcag tggcgcacca atggcagaca taacgagggc gccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcctc gaacgacaat cactactttg gctacagcac cccttggggg | 840 |
| tatttgact tcaacagatt ccactgccac ttttcaccac gtgactggca agactcatc | 900 |
| aacaacaact ggggattccg acccaagaga ctcaacttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcacctg | 1140 |
| aacaacggga gtcaggcagt aggacgctct tcattttact gcctggagta ctttccttct | 1200 |
| cagatgctgc gtaccggaaa caactttacc ttcagctaca cttttgagga cgttccttc | 1260 |
| cacagcagct acgctcacag ccagagtctg gaccgtctca tgaatcctct catcgaccag | 1320 |
| tacctgtatt acttgagcag aacaaacact ccaagtggaa ccaccacgca gtcaaggctt | 1380 |
| cagttttctc aggccggagc gagtgacatt cggaccagt ctaggaactg gcttcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt tccctcagag cggggttctc | 1620 |
| atctttggga agcaaggctc agagaaaaca aatgtggaca ttgaaaaggt catgattaca | 1680 |
| gacgaagagg aaatcaggac aaccaatccc gtggctacgg agcagtatgg ttctgtatct | 1740 |
| accaacctcc agagaggcaa caccggtaaa ctgggcgaca tagagtttat caaggtgaac | 1800 |

| | |
|---|---|
| aaaggcttaa gtagacaagc agctaccgca gatgtcaaca cacaaggcgt tcttccaggc | 1860 |
| atggtctggc aggacagaga tgtgtacctt caggggccca tctgggcaaa gattccacac | 1920 |
| acggacggac attttcaccc ctctcccctc atgggtggat tcggacttaa acaccctcct | 1980 |
| ccacagattc tcatcaagaa cacccggta cctgcgaatc cttcgaccac cttcagtgcg | 2040 |
| gcaaagtttg cttccttcat cacacagtac tccacgggac aggtcagcgt ggagatcgag | 2100 |
| tgggagctgc agaaggaaaa cagcaaacgc tggaatcccg aaattcagta cacttccaac | 2160 |
| tacaacaagt ctgttaatgt ggactttact gtggacacta atggcgtgta ttcagagcct | 2220 |
| cgccccattg gcaccagata cctgactcgt aatctgta | 2258 |

<210> SEQ ID NO 3
<211> LENGTH: 2246
<212> TYPE: DNA
<213> ORGANISM: Artificial Sequence
<220> FEATURE:
<223> OTHER INFORMATION: Synthetic

<400> SEQUENCE: 3

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg acccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt ggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg acccccagcc tctcggacag ccaccagcag cccctctgg tctgggaact | 600 |
| aatacgatgg ctacaggcag tggcgcacca atggcagaca taacgagg gccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcctc gaacgacaat cactactttg ctacagcac cccttggggg | 840 |
| tatttgact tcaacagatt ccactgccac ttttcaccac gtgactggca agactcatc | 900 |
| aacaacaact ggggattccg acccaagaga ctcaacttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga tcaggcagt aggacgctct tcattttact gcctggagta ctttcctcct | 1200 |
| cagatgctgc gtaccggaaa caactttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacaaacact ccaagtggag cccacatcgt gatggtggac | 1380 |
| gcctacaagc cgacgaagac caccacgcag tcaaggcttc agttttctca ggccggagcg | 1440 |
| agtgacattc gggaccagtc taggaactgg cttcctggac cctgttaccg ccagcagcga | 1500 |
| gtatcaaaga catctgcgga taacaacaac agtgaatact cgtggactgg agctaccaag | 1560 |
| taccacctca atggcagaga ctctctggtg aatccgggcc cggccatggc aagccacaag | 1620 |

-continued

```
gacgatgaag aaaagttttt tcctcagagc ggggttctca tctttgggaa gcaaggctca    1680
gagaaaacaa atgtggacat tgaaaaggtc atgattacag acgaagagga aatcaggaca    1740
accaatcccg tggctacgga gcagtatggt tctgtatcta ccaacctcca gagaggcaac    1800
agacaagcag ctaccgcaga tgtcaacaca caaggcgttc ttccaggcat ggtctggcag    1860
gacagagatg tgtaccttca ggggcccatc tgggcaaaga ttccacacac ggacggacat    1920
tttcacccct ctcccctcat gggtggattc ggacttaaac ccctcctcc acagattctc    1980 atcaagaaca ccccggtacc tgcgaatcct tcgaccacct tcagtgcggc aaagtttgct    2040
tccttcatca cacagtactc cacgggacag gtcagcgtgg agatcgagtg ggagctgcag    2100
aaggaaaaca gcaaacgctg gaatcccgaa attcagtaca cttccaacta caacaagtct    2160
gttaatgtgg actttactgt ggacactaat ggcgtgtatt cagagcctcg ccccattggc    2220
accagatacc tgactcgtaa tctgta                                        2246
```

<210> SEQ ID NO 4
<211> LENGTH: 2261
<212> TYPE: DNA
<213> ORGANISM: Artificial Sequence
<220> FEATURE:
<223> OTHER INFORMATION: Synthetic

<400> SEQUENCE: 4

```
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
cggcagctcg acagcggaga caacccgtac ctcaagtaca ccacgccgga cgcggagttt     300
caggagcgcc ttaaagaaga tacgtctttt ggggggcaacc tcggacgagc agtcttccag     360
gcgaaaaaga gggttcttga acctctgggc ctggttgagg aacctgttaa gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg accccagcc tctcggacag ccaccagcag cccctctgg tctgggaact       600 aatacgatgg ctacaggcag tggcgcacca atggcagaca taacgagggg cgccgacgga     660
gtgggtaatt cctcgggaaa ttggcattgc gattccacat ggatgggcga cagagtcatc     720
accaccagca cccgaacctg ggccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca aagactcatc     900
aacaacaact ggggattccg acccaagaga ctcaacttca gctctttaa cattcaagtc       960 aaagaggtca cgcagaatga cggtacgacg acgattgcca taaccttac cagcacggtt      1020 caggtgttta ctgactcgga gtaccagctc ccgtacgtcc tcggctcggc gcatcaagga    1080
tgcctcccgc cgttcccagc agacgtcttc atggtgccac agtatggata cctcaccctg    1140
aacaacggga gtcaggcagt aggacgctct tcatttact gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccggtgccca catcgtgatg    1380
```

| | | |
|---|---|---|
| gtggacgcct acaagccgac gaagggctta agtaccacca cgcagtcaag gcttcagttt | 1440 | |
| tctcaggccg gagcgagtga cattcgggac cagtctagga actggcttcc tggaccctgt | 1500 | |
| taccgccagc agcgagtatc aaagacatct gcggataaca caacagtga atactcgtgg | 1560 | |
| actggagcta ccaagtacca cctcaatggc agagactctc tggtgaatcc gggcccggcc | 1620 | |
| atggcaagcc acaaggacga tgaagaaaag ttttttcctc agagcggggt tctcatcttt | 1680 | |
| gggaagcaag gctcagagaa acaaatgtg acattgaaa aggtcatgat tacagacgaa | 1740 | |
| gaggaaatca ggacaaccaa tcccgtggct acggagcagt atggttctgt atctaccaac | 1800 | |
| ctccagagag gcaacagaca gcagctacc gcagatgtca acacacaagg cgttcttcca | 1860 | |
| ggcatggtct ggcaggacag agatgtgtac cttcaggggc ccatctgggc aaagattcca | 1920 | |
| cacacggacg gacattttca cccctctccc ctcatgggtg gattcggact taaacaccct | 1980 | |
| cctccacaga ttctcatcaa gaacaccccg gtacctgcga atccttcgac caccttcagt | 2040 | |
| gcggcaaagt ttgcttcctt catcacacag tactccacgg gacaggtcag cgtggagatc | 2100 | |
| gagtgggagc tgcagaagga aaacagcaaa cgctggaatc ccgaaattca gtacacttcc | 2160 | |
| aactacaaca gtctgttaa tgtggacttt actgtggaca ctaatggcgt gtattcagag | 2220 | |
| cctcgcccca ttggcaccag atacctgact cgtaatctgt a | 2261 | |

<210> SEQ ID NO 5
<211> LENGTH: 1842
<212> TYPE: DNA
<213> ORGANISM: Artificial Sequence
<220> FEATURE:
<223> OTHER INFORMATION: Synthetic

<400> SEQUENCE: 5

| | | |
|---|---|---|
| aggccggtag agcactctcc tgtggagcca gactcctcct cgggaaccgg aaaggcgggc | 60 | |
| cagcagcctg caagaaaaag attgaatttt ggtcagactg gagacgcaga ctcagtacct | 120 | |
| gacccccagc ctctcggaca gccaccagca gcccctctg gtctgggaac taatacgatg | 180 | |
| gctacaggca gtggcgcacc aatggcagac aataacgagg gcgccgacgg agtgggtaat | 240 | |
| tcctcgggaa attggcattg cgattccaca tggatgggcg acagagtcac caccaccagc | 300 | |
| acccgaacct gggccctgcc cacctacaac aaccacctct acaaacaaat tccagccaa | 360 | |
| tcaggagcct cgaacgacaa tcactacttt ggctacagca ccccttgggg gtattttgac | 420 | |
| ttcaacagat tccactgcca cttttcacca cgtgactggc aaagactcat caacaacaac | 480 | |
| tggggattcc gacccaagag actcaacttc aagctcttta acattcaagt caaagaggtc | 540 | |
| acgcagaatg acggtacgac gacgattgcc aataaccta ccagcacggt tcaggtgttt | 600 | |
| actgactcgg agtaccagct cccgtacgtc ctcggctcgg cgcatcaagg atgcctcccg | 660 | |
| ccgttcccag cagacgtctt catggtgcca cagtatggat acctcaccct gaacaacggg | 720 | |
| agtcaggcag taggacgctc ttcattttac tgcctggagt actttccttc tcagatgctg | 780 | |
| cgtaccggaa acaactttac cttcagctac actttgagg acgttccttt ccacagcagc | 840 | |
| tacgctcaca gccagagtct ggaccgtctc atgaatcctc tcatcgacca gtacctgtat | 900 | |
| tacttgagca gaacaaacac tccaagtgga accaccacgc agtcaaggct tcagttttct | 960 | |
| caggccggag cgagtgacat tcgggaccag tctaggaact ggcttcctgg accctgttac | 1020 | |
| cgccagcagc gagtatcaaa gacatctgcg gataacaaca acagtgaata ctcgtggact | 1080 | |
| ggagctacca gtaccaccct caatggcaga gactctctgg tgaatccggg cccggccatg | 1140 | |
| gcaagccaca aggacgatga agaaaagttt tttcctcaga gcggggttct catctttggg | 1200 | |

| | |
|---|---|
| aagcaaggct cagagaaaac aaatgtggac attgaaaagg tcatgattac agacgaagag | 1260 |
| gaaatcagga caaccaatcc cgtggctacg gagcagtatg gttctgtatc taccaacctc | 1320 |
| cagagaggca acagacaagc agctaccgca gatgtcaaca cacaaggcgt tcttccaggc | 1380 |
| atggtctggc aggacagaga tgtgtacctt caggggccca tctgggcaaa gattccacac | 1440 |
| acggacggac attttcaccc ctctcccctc atgggtggat tcggacttaa cacccctcct | 1500 |
| ccacagattc tcatcaagaa cacccccggta cctgcgaatc cttcgaccac cttcagtgcg | 1560 |
| gcaaagtttg cttccttcat cacacagtac tccacgggac aggtcagcgt ggagatcgag | 1620 |
| tgggagctgc agaaggaaaa cagcaaacgc tggaatcccg aaattcagta cacttccaac | 1680 |
| tacaacaagt ctgttaatgt ggactttact gtggacacta atggcgtgta ttcagagcct | 1740 |
| cgccccattg gcaccagata cctgactcgt aatctgggca gcggcggcag cggcggcagc | 1800 |
| ggcgcccaca tcgtgatggt ggacgcctac aagccgacga ag | 1842 |

<210> SEQ ID NO 6
<211> LENGTH: 1839
<212> TYPE: DNA
<213> ORGANISM: Artificial Sequence
<220> FEATURE:
<223> OTHER INFORMATION: Synthetic

<400> SEQUENCE: 6

| | |
|---|---|
| aggccggtag agcactctcc tgtggagcca gactcctcct cgggaaccgg aaaggcgggc | 60 |
| cagcagcctg caagaaaaag attgaatttt ggtcagactg gagacgcaga ctcagtacct | 120 |
| gacccccagc ctctcggaca gccaccagca gcccctctg gtctgggaac taatacgatg | 180 |
| gctacaggca gtggcgcacc aatggcagac aataacgagg gcgccgacgg agtgggtaat | 240 |
| tcctcgggaa attggcattg cgattccaca tggatgggcg acagagtcac caccaccagc | 300 |
| acccgaacct gggccctgcc cacctacaac aaccacctct acaaacaaat tccagccaa | 360 |
| tcaggagcct cgaacgacaa tcactacttt ggctacagca cccccttgggg gtattttgac | 420 |
| ttcaacagat tccactgcca cttttcacca cgtgactggc aaagactcat caacaacaac | 480 |
| tggggattcc gacccaagag actcaacttc aagctcttta acattcaagt caaagaggtc | 540 |
| acgcagaatg acggtacgac gacgattgcc aataacctta ccagcacggt tcaggtgttt | 600 |
| actgactcgg agtaccagct cccgtacgtc ctcggctcgg cgcatcaagg atgcctcccg | 660 |
| ccgttcccag cagacgtctt catggtgcca cagtatggat acctcaccct gaacaacggg | 720 |
| agtcaggcag taggacgctc ttcatttttac tgcctggagt actttccttc tcagatgctg | 780 |
| cgtaccggaa caactttac cttcagctac acttttgagg acgttccttt ccacagcagc | 840 |
| tacgctcaca gccagagtct ggaccgtctc atgaatcctc tcatcgacca gtacctgtat | 900 |
| tacttgagca gaacaaacac tccaagtgga accaccacgc agtcaaggct tcagttttct | 960 |
| caggccggag cgagtgacat tcgggaccag tctaggaact ggcttcctgg accctgttac | 1020 |
| cgccagcagc gagtatcaaa gacatctgcg gataacaaca cagtgaata tcgtggact | 1080 |
| ggagctacca gtaccaccct caatggcaga gactctctgg tgaatccggg cccggccatg | 1140 |
| gcaagccaca aggacgatga agaaaagttt tttcctcaga gcggggttct catctttggg | 1200 |
| aagcaaggct cagagaaaac aaatgtggac attgaaaagg tcatgattac agacgaagag | 1260 |
| gaaatcagga caaccaatcc cgtggctacg gagcagtatg gttctgtatc taccaacctc | 1320 |
| cagagaggca acagacaagc agctaccgca gatgtcaaca cacaaggcgt tcttccaggc | 1380 |

| | |
|---|---:|
| atggtctggc aggacagaga tgtgtacctt caggggccca tctgggcaaa gattccacac | 1440 |
| acggacggac attttcaccc ctctcccctc atgggtggat tcggacttaa acaccctcct | 1500 |
| ccacagattc tcatcaagaa caccccggta cctgcgaatc cttcgaccac cttcagtgcg | 1560 |
| gcaaagtttg cttccttcat cacacagtac tccacgggac aggtcagcgt ggagatcgag | 1620 |
| tgggagctgc agaaggaaaa cagcaaacgc tggaatcccg aaattcagta cacttccaac | 1680 |
| tacaacaagt ctgttaatgt ggactttact gtggacacta atggcgtgta ttcagagcct | 1740 |
| cgccccattg gcaccagata cctgactcgt aatctgggca gcggcggcag cggcggcagc | 1800 |
| ggcaaactgg gcgacataga gtttatcaag gtgaacaaa | 1839 |

<210> SEQ ID NO 7
<211> LENGTH: 2264
<212> TYPE: DNA
<213> ORGANISM: Artificial Sequence
<220> FEATURE:
<223> OTHER INFORMATION: Synthetic

<400> SEQUENCE: 7

| | |
|---|---:|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg acccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt ggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg accccagcc tctcggacag ccaccagcag ccccctctgg tctgggaact | 600 |
| aatacgatgg ctacaggcag tggcgcacca atggcagaca taacgagggg cgccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcctc gaacgacaat cactactttg ctacagcac ccttggggg | 840 |
| tattttgact tcaacagatt ccactgccac ttttcaccac gtgactggca agactcatc | 900 |
| aacaacaact ggggattccg acccaagaga ctcaacttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga tcaggcagt aggacgctct tcattttact gcctggagta ctttcctct | 1200 |
| cagatgctgc gtaccggaaa caactttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacaaacact ccaagtggaa ccaccacgca gtcaaggctt | 1380 |
| cagttttctc aggccggagc gagtgacatt cgggaccagt ctaggaactg gcttcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt tccctcagag cggggttctc | 1620 |

```
atctttggga agcaaggctc agagaaaaca aatgtggaca ttgaaaaggt catgattaca      1680
gacgaagagg aaatcaggac aaccaatccc gtggctacgg agcagtatgg ttctgtatct      1740
accaacctcc agagaggcaa caccggtgtg cctactatcg tgatggtgga cgcctacaag      1800
cgttacaagg gcttaagtag acaagcagct accgcagatg tcaacacaca aggcgttctt      1860
ccaggcatgg tctggcagga cagagatgtg taccttcagg ggcccatctg ggcaaagatt      1920
ccacacacgg acggacattt tcacccctct cccctcatgg gtggattcgg acttaaacac      1980
cctcctccac agattctcat caagaacacc ccggtacctg cgaatccttc gaccaccttc      2040
agtgcggcaa agtttgcttc cttcatcaca cagtactcca cgggacaggt cagcgtggag      2100
atcgagtggg agctgcagaa ggaaaacagc aaacgctgga atcccgaaat tcagtacact      2160
tccaactaca acaagtctgt taatgtggac tttactgtgg acactaatgg cgtgtattca      2220
gagcctcgcc ccattggcac cagataccctg actcgtaatc tgta                    2264
```

<210> SEQ ID NO 8
<211> LENGTH: 2264
<212> TYPE: DNA
<213> ORGANISM: Artificial Sequence
<220> FEATURE:
<223> OTHER INFORMATION: Synthetic

<400> SEQUENCE: 8

```
atggctgccg atggttatct tccagattgg ctcgaggaca ctctctctga aggaataaga        60
cagtggtgga agctcaaacc tggcccacca ccaccaaagc ccgcagagcg gcataaggac       120
gacagcaggg gtcttgtgct tcctgggtac aagtacctcg gacccttcaa cggactcgac       180
aagggagagc cggtcaacga ggcagacgcc gcggccctcg agcacgacaa agcctacgac       240
cggcagctcg acagcggaga acccgtac ctcaagtaca ccacgccga cgcggagttt         300
caggagcgcc ttaaagaaga tacgtctttt gggggcaacc tcggacgagc agtcttccag       360
gcgaaaaaga gggttcttga acctctgggc ctggttgagg aacctgttaa gacggctccg       420
ggaaaaaaga ggccggtaga gcactctcct gtggagccag actcctcctc gggaaccgga       480
aaggcgggcc agcagcctgc aagaaaaaga ttgaattttg gtcagactgg agacgcagac       540
tcagtacctg accccagcc tctcggacag ccaccagcag ccccctctgg tctgggaact       600
aatacgatgg ctacaggcag tggcgcacca atggcagaca taacgagggg cgccgacgga       660
gtgggtaatt cctcgggaaa ttggcattgc gattccacat ggatgggcga cagagtcatc       720
accaccagca cccgaacctg ggccctgccc acctacaaca accacctcta caaacaaatt       780
tccagccaat caggagcctc gaacgacaat cactactttg gctacagcac ccctgggggg       840
tattttgact tcaacagatt ccactgccac ttttcaccac gtgactggca agactcatc       900
aacaacaact ggggattccg acccaagaga ctcaacttca gctctttaa cattcaagtc       960
aaagaggtca gcagaatga cggtacgacg acgattgcca ataaccttac cagcacggtt      1020
caggtgttta ctgactcgga gtaccagctc ccgtacgtcc tcggctcggc gcatcaagga      1080
tgcctcccgc cgttcccagc agacgtcttc atggtgccac agtatggata cctcacactg      1140
aacaacggga gtcaggcagt aggacgctct tcattttact gcctggagta ctttcccttct      1200
cagatgctgc gtaccggaaa caacttacc ttcagctaca cttttgagga cgttcctttc       1260
cacagcagct acgctcacag ccagagtctg gaccgtctca tgaatcctct catcgaccag      1320
tacctgtatt acttgagcag aacaaacact ccaagtggaa ccggtgtgcc tactatcgtg      1380
```

| | |
|---|---|
| atggtggacg cctacaagcg ttacaagggc ttaagtacca ccacgcagtc aaggcttcag | 1440 |
| ttttctcagg ccggagcgag tgacattcgg gaccagtcta ggaactggct tcctggaccc | 1500 |
| tgttaccgcc agcagcgagt atcaaagaca tctgcggata caacaacag tgaatactcg | 1560 |
| tggactggag ctaccaagta ccacctcaat ggcagagact ctctggtgaa tccgggcccg | 1620 |
| gccatggcaa gccacaagga cgatgaagaa aagttttttc ctcagagcgg ggttctcatc | 1680 |
| tttgggaagc aaggctcaga gaaaacaaat gtggacattg aaaaggtcat gattacagac | 1740 |
| gaagaggaaa tcaggacaac caatcccgtg gctacggagc agtatggttc tgtatctacc | 1800 |
| aacctccaga gaggcaacag acaagcagct accgcagatg tcaacacaca aggcgttctt | 1860 |
| ccaggcatgg tctggcagga cagagatgtg taccttcagg ggcccatctg gcaaagatt | 1920 |
| ccacacacgg acggacattt tcacccctct cccctcatgg gtggattcgg acttaaacac | 1980 |
| cctcctccac agattctcat caagaacacc ccggtacctg cgaatccttc gaccaccttc | 2040 |
| agtgcggcaa agtttgcttc cttcatcaca cagtactcca cgggacaggt cagcgtggag | 2100 |
| atcgagtggg agctgcagaa ggaaaacagc aaacgctgga tcccgaaat tcagtacact | 2160 |
| tccaactaca caagtctgt taatgtggac tttactgtgg acactaatgg cgtgtattca | 2220 |
| gagcctcgcc ccattggcac cagatacctg actcgtaatc tgta | 2264 |

<210> SEQ ID NO 9
<211> LENGTH: 2136
<212> TYPE: DNA
<213> ORGANISM: Artificial Sequence
<220> FEATURE:
<223> OTHER INFORMATION: Synthetic

<400> SEQUENCE: 9

| | |
|---|---|
| gccaccatgg gctcaggtga tagtgctacc catattaaat tctcaaaacg tgatgaggac | 60 |
| ggcaaagagt tagctggtgc aactatggag ttgcgtgatt catctggtaa aactattagt | 120 |
| acatggattt cagatggaca agtgaaagat ttctacctgt atccaggaaa atatacattt | 180 |
| gtcgaaaccg cagcaccaga cggttatgag gtagcaactg ctattacctt tacagttaat | 240 |
| gagcaaggtc aggttactgt aaatggcaaa gcaactaaag gtgacgctca tatttcaggt | 300 |
| ggtggcggtt caggcggagg tggctctggc ggtggcggat cggctccggg aaaaaagagg | 360 |
| ccggtagagc actctcctgt ggagccagac tcctcctcgg gaaccggaaa ggcgggccag | 420 |
| cagcctgcaa gaaaaagatt gaattttggt cagactggag acgcagactc agtacctgac | 480 |
| ccccagcctc tcggacagcc accagcagcc ccctctggtc tgggaactaa tacgatggct | 540 |
| acaggcagtg gcgcaccaat ggcagacaat aacgagggcg ccgacggagt gggtaattcc | 600 |
| tcgggaaatt ggcattgcga ttccacatgg atgggcgaca gagtcatcac caccagcacc | 660 |
| cgaacctggg ccctgcccac ctacaacaac cacctctaca acaaatttc agccaatca | 720 |
| ggagcctcga cgacaatca ctactttggc tacagcaccc cttggggta ttttgacttc | 780 |
| aacagattcc actgccactt tcaccacgt gactggcaaa gactcatcaa caacaactgg | 840 |
| ggattccgac ccaagagact caactttcaag ctctttaaca ttcaagtcaa agaggtcacg | 900 |
| cagaatgacg gtacgacgac gattgccaat aaccttacca gcacggttca ggtgtttact | 960 |
| gactcggagt accagctccc gtacgtcctc ggctcggcgc atcaaggatg cctcccgccg | 1020 |
| ttcccagcag acgtcttcat ggtgccacag tatggatacc tcaccctgaa caacgggagt | 1080 |
| caggcagtag gacgctcttc attttactgc ctggagtact tccttctca gatgctgcgt | 1140 |
| accggaaaca actttacctt cagctacact tttgaggacg ttcctttcca cagcagctac | 1200 |

```
gctcacagcc agagtctgga ccgtctcatg aatcctctca tcgaccagta cctgtattac   1260
ttgagcagaa caaacactcc aagtggaacc accacgcagt caaggcttca gttttctcag   1320
gccggagcga gtgacattcg ggaccagtct aggaactggc ttcctggacc ctgttaccgc   1380
cagcagcgag tatcaaagac atctgcggat aacaacaaca gtgaatactc gtggactgga   1440
gctaccaagt accacctcaa tggcagagac tctctggtga atccgggccc ggccatggca   1500
agccacaagg acgatgaaga aaagtttttt cctcagagcg gggttctcat ctttgggaag   1560
caaggctcag agaaaacaaa tgtggacatt gaaaaggtca tgattacaga cgaagaggaa   1620
atcaggacaa ccaatcccgt ggctacggag cagtatggtt ctgtatctac caacctccag   1680
agaggcaaca gacaagcagc taccgcagat gtcaacacac aaggcgttct tccaggcatg   1740
gtctggcagg acagagatgt gtaccttcag gggcccatct gggcaaagat tccacacacg   1800
gacggacatt ttcacccctc tcccctcatg ggtggattcg gacttaaaca ccctcctcca   1860
cagattctca tcaagaacac cccggtacct gcgaatcctt cgaccacctt cagtgcggca   1920
aagtttgctt ccttcatcac acagtactcc acgggacagg tcagcgtgga gatcgagtgg   1980
gagctgcaga aggaaaacag caaacgctgg aatcccgaaa ttcagtacac ttccaactac   2040
aacaagtctg ttaatgtgga ctttactgtg gacactaatg gcgtgtattc agagcctcgc   2100
cccattggca ccagatacct gactcgtaat ctgtaa                            2136

<210> SEQ ID NO 10
<211> LENGTH: 5784
<212> TYPE: DNA
<213> ORGANISM: Artificial Sequence
<220> FEATURE:
<223> OTHER INFORMATION: Synthetic

<400> SEQUENCE: 10
catcaccatc accatcacga gaacctctat ttccagggat cttctatgaa aatcgaagaa   60
ggtaaactgg taatctggat taacggcgat aaaggctata acggtctcgc tgaagtcggt   120
aagaaattcg agaaagatac cggaattaaa gtcaccgttg agcatccgga taaactggaa   180
gagaaattcc cacaggttgc ggcaactggc gatggccctg acattatctt ctgggcacac   240
gaccgctttg gtggctacgc tcaatctggc ctgttggctg aaatcacccc ggacaaagcg   300
ttccaggaca agctgtatcc gtttacctgg gatgccgtac gttacaacgg caagctgatt   360
gcttacccga tcgctgttga agcgttatcg ctgatttata caaagatctg ctgccgaac   420 ccgccaaaaa cctgggaaga gatcccggcg ctggataaag aactgaaagc gaaaggtaag   480
agcgcgctga tgttcaacct gcaagaaccg tacttcacct ggccgctgat tgctgctgac   540
gggggttatg cgttcaagta tgaaaacggc aagtacgaca ttaaagacgt gggcgtggat   600
aacgctggcg cgaaagcggg tctgaccttc ctggttgacc tgattaaaaa caaacacatg   660
aatgcagaca ccgattactc catcgcagaa gctgccttta taaaggcga acagcgatg   720 accatcaacg gcccgtgggc atggtccaac atcgacacca gcaaagtgaa ttatggtgta   780
acggtactgc cgaccttcaa gggtcaacca tccaaaccgt tcgttggcgt gctgagcgca   840
ggtattaacg ccgccagtcc gaacaaagag ctggcaaag agttcctcga aaactatctg   900
ctgactgatg aaggtctgga agcggttaat aaagacaaac cgctgggtgc cgtagcgctg   960
aagtcttacg aggaagagtt ggcgaaagat ccacgtattg ccgccactat ggaaaacgcc   1020
cagaaaggtg aaatcatgcc gaacatcccg cagatgtccg ctttctggta tgccgtgcgt   1080
```

```
actgcggtga tcaacgccgc cagcggtcgt cagactgtcg atgaagccct gaaagacgcg      1140
cagactaatt cgagctcgaa caacaacaac aataacaata acaacaacct cgggatcgag      1200
gaaaacctgt acttccaatc caatgccacc atggataaga aatactcaat aggcttagat      1260
atcggcacaa atagcgtcgg atgggcggtg atcactgatg aatataaggt tccgtctaaa      1320
aagttcaagg ttctgggaaa tacagaccgc cacagtatca aaaaaatct tatagggct       1380 cttttatttg acagtggaga gacagcgaa gcgactcgtc tcaaacggac agctcgtaga      1440
aggtatacac gtcggaagaa tcgtatttgt tatctacagg atttttttc aaatgagatg      1500 gcgaaagtag atgatagttt ctttcatcga cttgaagagt cttttttggt ggaagaagac      1560
aagaagcatg aacgtcatcc tattttggga aatatagtag atgaagttgc ttatcatgag      1620
aaatatccaa ctatctatca tctgcgaaaa aaattggtag attctactga taaagcggat      1680
ttgcgcttaa tctatttggc cttagcgcat atgattaagt ttcgtggtca ttttttgatt      1740
gagggagatt taaatcctga taatagtgat gtggacaaac tatttatcca gttggtacaa      1800
acctacaatc aattatttga agaaaaccct attaacgcaa gtggagtaga tgctaaagcg      1860
attctttctg cacgattgag taaatcaaga cgattagaaa atctcattgc tcagctcccc      1920
ggtgagaaga aaaatggctt atttgggaat ctcattgctt tgtcattggg tttgaccct      1980 aattttaaat caaattttga tttggcagaa gatgctaaat tacagctttc aaaagatact      2040
tacgatgatg atttagataa tttattggcg caaattggag atcaatatgc tgatttgttt      2100
ttggcagcta agaatttatc agatgctatt ttactttcag atatcctaag agtaaatact      2160
gaaataacta aggctccct atcagcttca atgattaaac gctacgatga acatcatcaa      2220
gacttgactc tttttaaaagc tttagttcga caacaacttc cagaaaagta taagaaatc      2280 tttttttgatc aatcaaaaaa cggatatgca ggttatattg atgggggagc tagccaagaa      2340
gaattttata aatttatcaa accaatttta gaaaaatgg atggtactga ggaattattg      2400
gtgaaactaa atcgtgaaga tttgctgcgc aagcaacgga cctttgacaa cggctctatt      2460
ccccatcaaa ttcacttggg tgagctgcat gctattttga aagacaagaa agacttttat      2520 ccattttaa aagacaatcg tgagaagatt gaaaaaatct tgacttttcg aattccttat      2580
tatgttggtc cattggcgcg tggcaatagt cgttttgcat ggatgactcg gaagtctgaa      2640
gaaacaatta ccccatggaa ttttgaagaa gttgtcgata aggtgcttc agctcaatca      2700 tttattgaac gcatgacaaa ctttgataaa aatcttccaa atgaaaaagt actaccaaaa      2760
catagtttgc tttatgagta ttttacggtt tataacgaat tgacaaaggt caaatatgtt      2820
actgaaggaa tgcgaaaacc agcatttctt tcaggtgaac agaagaaagc cattgttgat      2880
ttactcttca aaacaaatcg aaaagtaacc gttaagcaat aaaagaaga ttatttcaaa      2940 aaaatagaat gttttgatag tgttgaaatt tcaggagttg aagatagatt taatgcttca      3000 ttaggtaccct accatgattt gctaaaaatt attaaagata aagattttt ggataatgaa      3060 gaaaatgaag atatcttaga ggatattgtt ttaacattga ccttatttga agataggag      3120 atgattgagg aaagacttaa acatatgct cacctctttg atgataaggt gatgaaacag      3180
cttaaacgtc gccgttatac tggttgggga cgtttgtctc gaaaattgat taatggtatt      3240
agggataagc aatctggcaa aacaatatta gatttttga aatcagatgg ttttgccaat      3300
cgcaatttta tgcagctgat ccatgatgat agtttgacat ttaaagaaga cattcaaaaa      3360
gcacaagtgt ctggacaagg cgatagttta catgaacata ttgcaaattt agctggtagc      3420
cctgctatta aaaaaggtat tttacagact gtaaaagttg ttgatgaatt ggtcaaagta      3480
```

```
atgggggcggc ataagccaga aaatatcgtt attgaaatgg cacgtgaaaa tcagacaact    3540
caaaagggcc agaaaaattc gcgagagcgt atgaaacgaa tcgaagaagg tatcaaagaa    3600
ttaggaagtc agattcttaa agagcatcct gttgaaaata ctcaattgca aaatgaaaag    3660
ctctatctct attatctcca aaatggaaga gacatgtatg tggaccaaga attagatatt    3720
aatcgtttaa gtgattatga tgtcgatcac attgttccac aaagtttcct taaagacgat    3780
tcaatagaca ataaggtctt aacgcgttct gataaaaatc gtggtaaatc ggataacgtt    3840
ccaagtgaag aagtagtcaa aaagatgaaa aactattgga gacaacttct aaacgccaag    3900
ttaatcactc aacgtaagtt tgataattta acgaaagctg aacgtggagg tttgagtgaa    3960
cttgataaag ctggttttat caaacgccaa ttggttgaaa ctcgccaaat cactaagcat    4020
gtggcacaaa ttttggatag tcgcatgaat actaaatacg atgaaaatga taacttatt    4080 cgagaggtta aagtgattac cttaaaatct aaattagttt ctgacttccg aaaagatttc    4140
caattctata aagtacgtga gattaacaat taccatcatg cccatgatgc gtatctaaat    4200
gccgtcgttg gaactgcttt gattaagaaa tatccaaaac ttgaatcgga gtttgtctat    4260
ggtgattata aagtttatga tgttcgtaaa atgattgcta agtctgagca agaaataggc    4320
aaagcaaccg caaaatattt cttttactct aatatcatga acttcttcaa aacagaaatt    4380
acacttgcaa atgagagat cgcaaacgc cctctaatcg aaactaatgg ggaaactgga    4440
gaaattgtct gggataaagg gcgagatttt gccacagtgc gcaaagtatt gtccatgccc    4500
caagtcaata ttgtcaagaa aacagaagta cagacaggcg gattctccaa ggagtcaatt    4560
ttaccaaaaa gaaattcgga caagcttatt gctcgtaaaa aagactggga tccaaaaaaa    4620
tatggtggtt ttgatagtcc aacggtagct tattcagtcc tagtggttgc taaggtggaa    4680
aaagggaaat cgaagaagtt aaaatccgtt aaagagttac tagggatcac aattatggaa    4740
agaagttcct ttgaaaaaaa tccgattgac tttttagaag ctaaaggata taggaagtt    4800 aaaaaagact taatcattaa actacctaaa tatagtcttt ttgagttaga aaacggtcgt    4860
aaacggatgc tggctagtgc cggagaatta caaaaaggaa atgagctggc tctgccaagc    4920
aaatatgtga atttttata tttagctagt cattatgaaa agttgaaggg tagtccagaa    4980
gataacgaac aaaaacaatt gtttgtggag cagcataagc attatttaga tgagattatt    5040
gagcaaatca gtgaatttc taagcgtgtt attttagcag atgccaattt agataaagtt    5100
cttagtgcat ataacaaaca tagagacaaa ccaatacgtg aacaagcaga aaatattatt    5160
catttattta cgttgacgaa tcttggagct cccgctgctt ttaaatattt tgatacaaca    5220
attgatcgta acgatatac gtctacaaaa gaagttttag atgccactct tatccatcaa    5280
tccatcactg gtctttatga aacacgcatt gatttgagtc agctaggagg tgacgggtca    5340
cctaagaaaa aacgaaaagt tgaggatcct aaaaagaaac gaaagttga tggcagcggc    5400 ggcagcggcg gcagcggcgg cgccatggta accaccttat caggtttatc aggtgagcaa    5460
ggtccgtccg gtgatatgac aactgaagaa gatagtgcta cccatattaa attctcaaaa    5520
cgtgatgagg acggccgtga gttagctggt gcaactatgg agttgcgtga ttcatctggt    5580
aaaactatta gtacatggat ttcagatgga catgtgaagg atttctacct gtatccagga    5640
aaatatacat ttgtcgaaac cgcagcacca gacggttatg aggtagcaac tgctattacc    5700
tttacagtta atgagcaagg tcaggttact gtaaatggcg aagcaactaa aggtgacgct    5760
catactggat ccagtggtag ctaa    5784
```

<210> SEQ ID NO 11
<211> LENGTH: 1146
<212> TYPE: DNA
<213> ORGANISM: Artificial Sequence
<220> FEATURE:
<223> OTHER INFORMATION: Synthetic

<400> SEQUENCE: 11

```
catcaccatc accatcacga gaacctctat ttccagggag tgagcaaggg cgaggagctg      60
ttcaccgggg tggtgcccat cctggtcgag ctggacggcg acgtaaacgg ccacaagttc     120
agcgtccgcg gcgagggcga gggcgatgcc accaacggca agctgaccct gaagttcatc     180
tgcaccaccg gcaagctgcc cgtgccctgg cccacccctcg tgaccacctt cggctacggc     240
gtggcctgct tcagccgcta ccccgaccac atgaagcagc acgacttctt caagtccgcc     300
atgcccgaag gctacgtcca ggagcgcacc atctctttca aggacgacgg tacctacaag     360
acccgcgccg aggtgaagtt cgagggcgac accctggtga accgcatcga gctgaagggc     420
atcgacttca aggaggacgg caacatcctg ggcacaagc tggagtacaa cttcaacagc     480
cactacgtct atatcaccggc cgacaagcag aagaactgca tcaaggctaa cttcaagatc     540
cgccacaacg ttgaggacgg cagcgtgcag ctcgccgacc actaccagca gaacaccccc     600
atcggcgacg gccccgtgct gctgcccgac aaccactacc tgagccatca gtccaagctg     660
agcaaagacc ccaacgagaa gcgcgatcac atggtcctgc tggagttcgt gaccgccgcc     720
gggattacac atggcatgga cgagctgtac aagggcagcg gcggcagcgg cggcagcggc     780
ggcgccatgg taaccacctt atcaggttta tcaggtgagc aagtccgtc cggtgatatg     840
acaactgaag aagatagtgc tacccatatt aaattctcaa aacgtgatga ggacggccgt     900
gagttagctg gtgcaactat ggagttgcgt gattcatctg gtaaaactat tagtacatgg     960
atttcagatg gacatgtgaa ggatttctac ctgtatccag gaaaatatac atttgtcgaa    1020
accgcagcac cagacggtta tgaggtagca actgctatta cctttacagt taatgagcaa    1080
ggtcaggtta ctgtaaatgg cgaagcaact aaaggtgacg ctcatactgg atccagtggt    1140
agctaa                                                                1146
```

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12

```
uagagcguga ggaaguugau                                                   20
```

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13

```
aggccttcgc agcattctt                                                    19
```

<210> SEQ ID NO 14
<211> LENGTH: 20
<212> TYPE: DNA
<213> ORGANISM: Artificial Sequence

```
<220> FEATURE:
<223> OTHER INFORMATION: Synthetic

<400> SEQUENCE: 14
gcagcacccc atctgttttc                                              20
```

CONJUGATES COMPRISING AAVS AND CAS9 POLYPEPTIDES

CROSS-REFERENCE TO RELATED APPLICATIONS

This patent application is a National Stage application under 35 U.S.C. § 371 of International Application No. PCT/US2019/020096, filed on Feb. 28, 2019, which claims the benefit of priority to U.S. Patent Application No. 62/636,638, filed on Feb. 28, 2018. The disclosures of the prior applications are considered part of (and are incorporated by reference in) the disclosure of this application.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,315 Byte ASCII (Text) file named "741805_ST25.TXT," dated Feb. 28, 2019.

BACKGROUND OF THE INVENTION

Currently, viruses, such as adeno-associated virus (AAV), are the most efficient mode for in vivo gene transfer but they do not often allow for temporal control of protein expression. Instead, genes delivered via viral vectors often are permanently expressed, a significant drawback in cases such as Cas9, where sustained expression leads to off-target effects. Inducible promoters can provide a level of transience but are often leaky or inefficient.

AAVs are highly efficient non-pathogenic vectors for in vivo gene delivery, have strong tropism for neural cells, and are easy to produce and work with in a laboratory setting. However, the size of the AAV vector is severely restricted to 4.7 kB, prohibiting delivery of large or multiple genes. Accordingly, there is a need for improved AAV-based vector systems that allow for delivery of larger transgenes than can be accommodated in a single AAV virion. Also, a need exists for an AAV-based vector that can deliver proteins, such as Cas9, for which transient expression is important.

BRIEF SUMMARY OF THE INVENTION

The invention provides an innovative gene and protein delivery system, building on the safety and efficiency of AAVs, that overcomes these major obstacles to in vivo gene delivery. In order to overcome packaging size limits and permanent protein expression, the invention provides a modular AAV-based gene and protein delivery system using a peptide tag that spontaneously forms a bond (a non-limiting example of which can be a covalent bond) that is unbreakable under physiologically relevant conditions with a small globular protein. By expressing this peptide tag on the surface of the AAV virion and expressing a binding-partner on either another AAV or another protein, the inventive AAV vector can link (such as, for example, covalently link) capsids to each other and/or to proteins, creating a larger infectious unit. This highly flexible, expandable and modular system for delivery of genes and proteins into cells greatly expands the capabilities of AAV for gene and protein delivery.

By linking together AAV capsids to form conjugates, the present invention can double (or more than double) the carrying capacity of AAV vectors, enabling delivery of large genes and multiple genes through obligate AAV coinfection. Furthermore, by tethering proteins to the outside of the AAV capsid, the present invention harnesses the tropism and infectivity of the virus while delivering biologically active proteins, such as Cas9, where transient expression is essential.

The present invention also can be expanded to combine these two approaches, allowing co-delivery of groupings of genes and proteins. Together this approach overcomes some of the most significant barriers to in vivo gene and protein delivery and expands the utility of AAV-mediated gene delivery and gene editing for biological research and gene therapy. Importantly, this system of the present invention is modular, highly flexible, and can be modified for a wide variety of experimental purposes. The development of this system of the present invention has widespread implications for all areas of biology, opens up new therapeutic avenues for diseases involving large genes or requiring transient expression, and opens new avenues of research for scientists across disciplines by providing customizable tools for precise and efficient control of in vivo gene expression, gene editing, and protein delivery. Also, the concepts and methods here are expandable and could be transferred to other types of virus.

In one embodiment, the invention provides an Adeno-Associated Virus (AAV) comprising an exterior surface, which surface comprises one or more peptide tags that form a bond (a non-limiting example of which can be a covalent bond) with a binding-partner, wherein the AAV is a live virus. In another embodiment, the invention provides a conjugate comprising at least one such AAV and at least one polypeptide comprising a first domain which is the binding-partner for the tag and a second domain, which is a bioactive polypeptide, wherein the AAV and the polypeptide are bound (such as, for example, covalently bound). In another embodiment, the invention provides a conjugate comprising at least one such AAV (first AAV) and at least one second AAV, which second AAV comprises a second exterior surface, which second exterior surface comprises at least one binding-partner for the tag or for a third linker molecule, wherein the at least one first AAV and the at least one second AAV are bound (such as, for example, covalently bound), and wherein the at least one second AAV is a live virus.

The invention also provides methods of infecting cells with the inventive AAV and conjugates, and compositions comprising the inventive AAV and conjugates and a cell, in which the cell is infected with the inventive AAV or conjugate. The invention also provides a pharmaceutical composition comprising the inventive AAV or conjugate and a pharmaceutically-acceptable carrier.

BRIEF DESCRIPTION OF THE SEVERAL VIEWS OF THE DRAWING(S)

FIG. 1 presents schematic illustrations of the inventive approach. Row A concerns linked viruses (AAV). A peptide tag is expressed on the surface of the AAV capsid, and a protein binding-partner is expressed on another virus (second AAV). Mixing these two virus species together, the linker pair spontaneously forms a bond (a non-limiting example of which can be a covalent bond) that is permanently stable under physiological conditions, leading to the formation of conjugate (depicted as a virus dimer in Row A), increasing the carrying capacity of the vector and allowing for precise control of the ratios of genes delivered. The conjugate enables delivery of multiple genes to the same cell, or delivery of large genes through obligate co-infection followed by recombination. Row B concerns the linking of 2 virus capsids that via a third linker molecule, where the linker is comprised of molecules that bind to linkers on both viruses and bridges the two vectors together. Row C concerns proteins linked to viruses to form conjugates. By tethering proteins to the outside of the capsid, the tropism and infectivity of AAV can be harnessed to deliver therapeutic proteins, such as Cas9, non-permanently. Transient expression of Cas9 is essential to reducing off-target effects. Linked functional proteins are delivered into the nucleus, perform their action, and then degrade. Row D represents how the inventive approach can be expanded. Combining these approaches, any string of DNA-containing viral particles and proteins can be delivered together as a multimeric conjugate unit.

Figure 2:
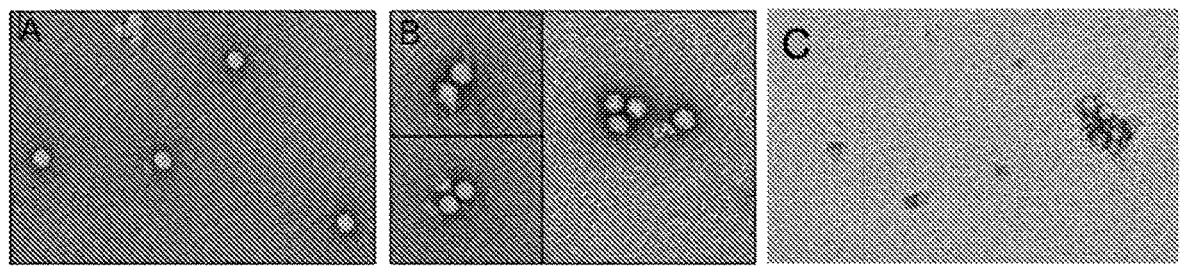

FIG. 2 presents electron microscopy images of linked vectors (AAV conjugates). Panel A shows AAV2 vectors as control. Panel B presents data demonstrating that AAV2-SpyTag vectors linked to with AAV2-SnoopTag vectors to form multi-viral conjugates. The conjugates appear as dimers or trimers of AAV virions. Panel C shows that overexpression of SpyTag/SnoopTag linkers cause the formation of a clump of AAV capsids, in which many AAV vectors are tethered together.

Figure 3:
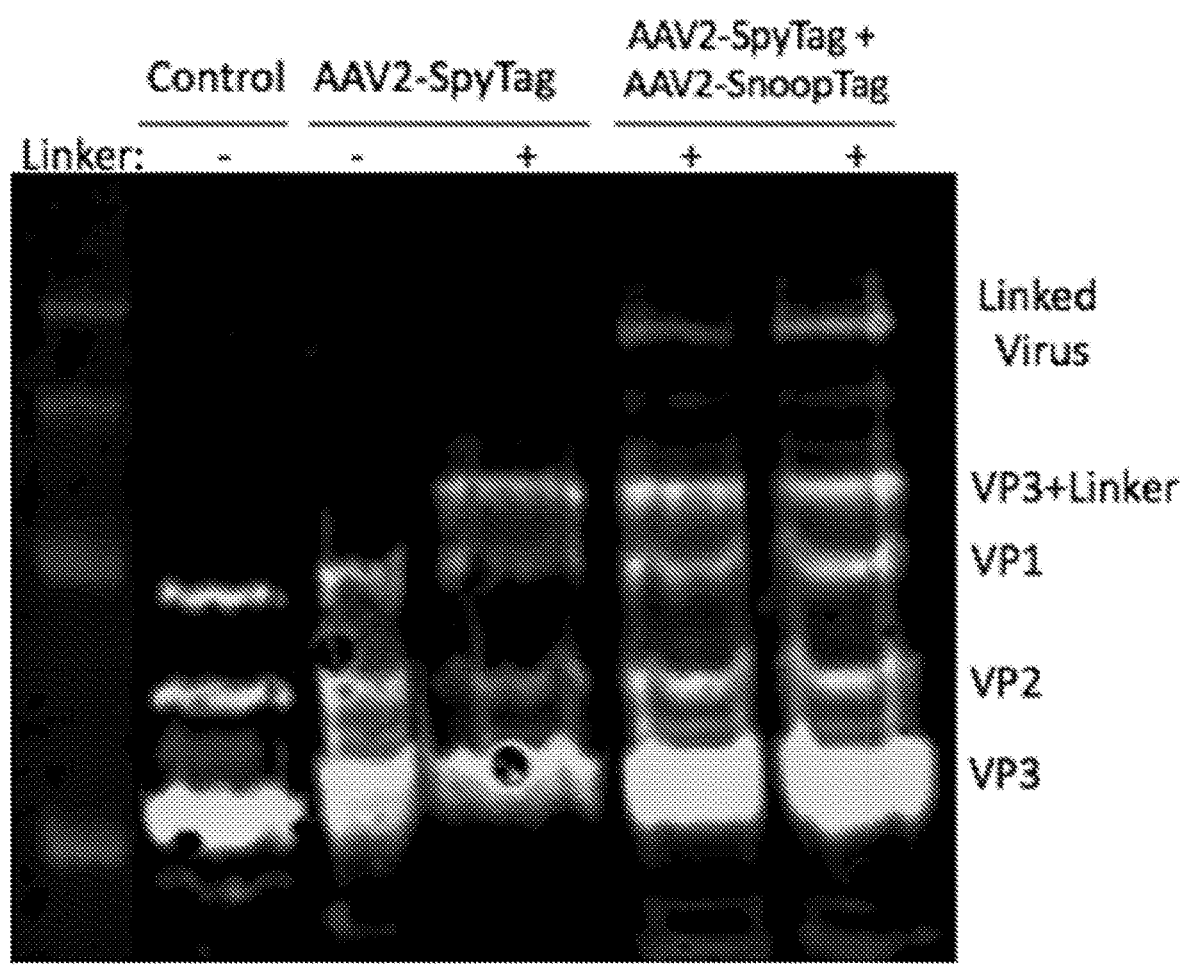

FIG. 3 depicts a Western blot image showing the linking of AAV capsids. The upper band in the last two lanes is indicative of linked VP3 subunits. In this particular embodiment, the AAV capsids were linked via a third linking molecule ((VP3SpyTag-Linker-VP3SnoopTag) (FIG. 1, Row B).

Figure 4:
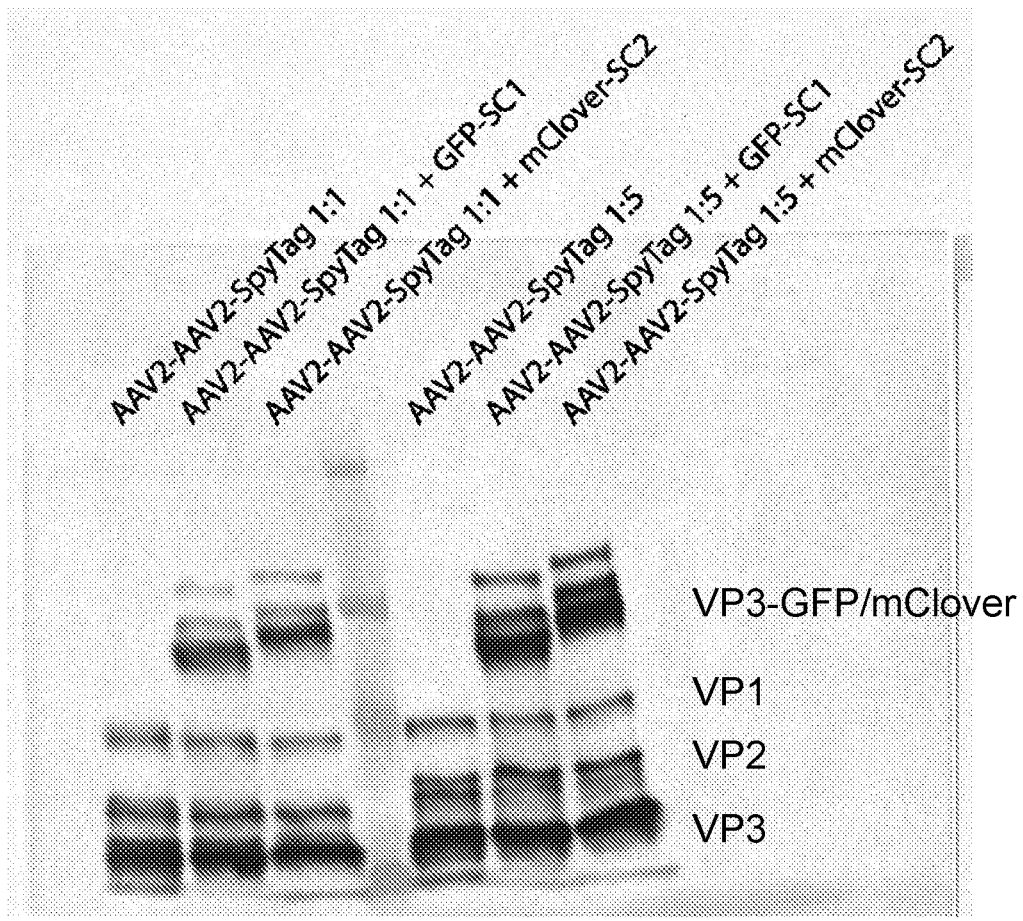
Figure 4:
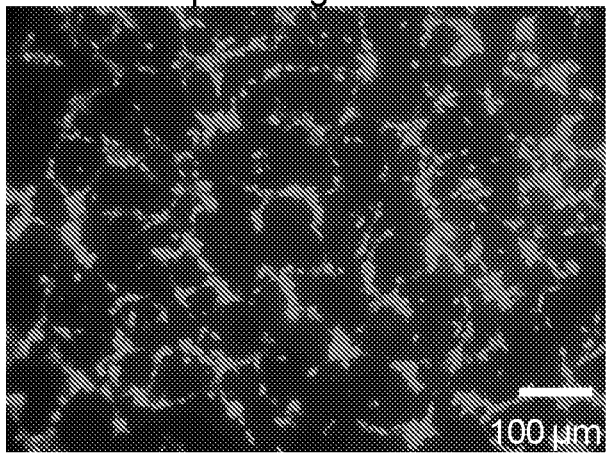
Figure 4:
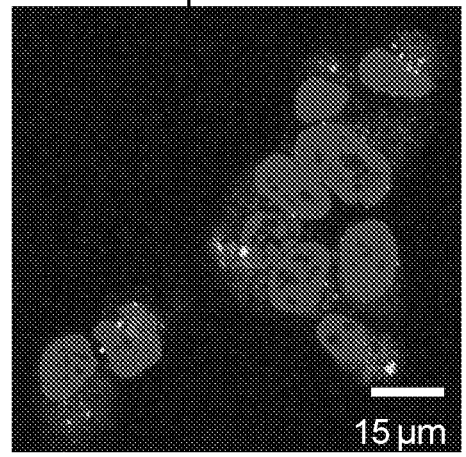

FIG. 4 graphically depicts conjugates comprising AAV's linked to functional protein. Panel A depicts increasing amounts of GFP-SpyCatcher are linked to the AAV-SpyTag. Panel B depicts expression of tdTomato (encoded by a transgene packaged into AAV2), demonstrating that AAV-SpyTag-GFP-SpyCatcher is infectious. Panel C presents data demonstrating that AAV-SpyTag-GFP-SpyCatcher particles can be tracked by super-resolution confocal microscopy, demonstrating successful incorporation of functional protein.

Figure 5:
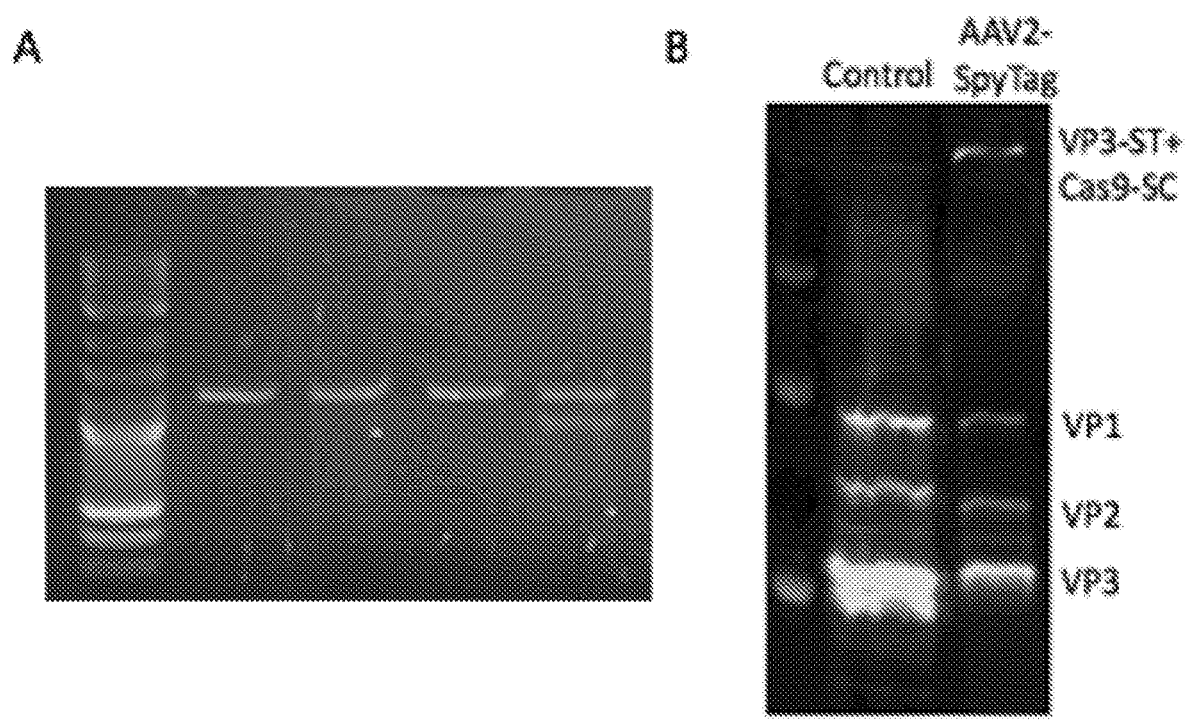

FIG. 5 presents data concerning an AAV-polypeptide conjugate in which Cas9-SpyCatcher was covalently bound to AAV2-SpyTag. Panel A concerns HEK293T cells that were transfected with Cas9-Spycatcher and a guide RNA targeting Rhodopsin. CRISPR/Cas9 induced mutations were tested by T7 assay. The first two lanes show untransfected samples as 1) untreated and 2) treated with T7 Endonuclease. The last two lanes show transfected samples as 3) untreated and 4) treated with T7 Endonuclease. The Cas9-Spycatcher cleaved product can be seen in the fourth lane. Panel B presents a Western blot image showing the binding of AAV2-SpyTag to Cas9-SpyCatcher.

DETAILED DESCRIPTION OF THE INVENTION

In an embodiment, the invention provides an AAV comprising an exterior surface, which surface comprises one or more peptide tags that form a bond (a non-limiting example of which can be a covalent bond) with a binding-partner. In the context of the present invention, the AAV preferably is a live virus, as opposed to a virus-like particle (VLP).

The peptide tag is a polypeptide that can form a bond with a binding-partner. This ensures that, once the inventive AAV forms such a bond, the bond is stable and generally unbreakable under physiologically relevant conditions, so that the AAV delivers whatever is tethered (for example, a second AAV, a bioactive polypeptide, etc.) to a cell via the tag-binding-partner bond upon infection.

The "tag" in the context of the invention can be any suitable polypeptide that can form a bond (a non-limiting example of which can be a covalent bond) to a specific binding-partner when expressed on the exterior surface of the AAV. Examples of suitable tags include, but are not limited to bacteria-derived molecular tethers called SpyTag and its binding-partner SpyCatcher or SnoopTag and its binding-partner SnoopCatcher, or SpyTag002 and its binding-partner, SpyCatcher002 (see, e.g., Zakeri, B. et al. Peptide tag forming a rapid covalent bond to a protein, through engineering a bacterial adhesin. *Proceedings of the National Academy of Sciences* 109, E690-7 (2012) (incorporated herein in its entirety by reference) and Veggiani, G. et al. Programmable polyproteins built using twin peptide superglues. *Proc. Natl. Acad. Sci. U.S.A* 113, 1202-1207 (2016) (incorporated herein in its entirety by reference) and Keeble et al. Evolving Accelerated Amidation by SpyTag/SpyCatcher to Analyze Membrane Dynamics. Angew Chem Int Ed Engl. (2017) (incorporated herein in its entirety by reference)). Typically, the bond (tether) is a covalent bond; however, other tethers can be used. Other molecular tethers that could be used include, for example, split inteins (see, e.g. Wu et al. Protein trans-splicing by a split intein encoded in a split DnaE gene of *Synechocystis* sp. PCC6803. PNAS (1998)(incorporated herein in its entirety by reference)), sortase (see, e.g. Kobashigawa et al., Attachment of an NMR-invisible solubility enhancement tag using a sortase-mediated protein ligation method. J Biomol NMR. (2009) (incorporated herein in its entirety by reference)), split GFP (see e.g. Feinberg, E. H. et al. GFP reconstitution across synaptic partners (GRASP) defines cell contacts and synapses in living nervous systems. Neuron 57, 353-363 (2008) (incorporated herein in its entirety by reference)), or other similar linker molecules.

The tag can be engineered to be expressed on the surface of the inventive AAV by mutating the genetic sequence encoding AAV polypeptides having extracellular domains to include such tags. For example, the AAV VP2 and VP3 polypeptides are suitable polypeptides to mutate to include such a tag domain. Suitable sites for inclusion of the tag include positions 453, 588 of AAV2 VP3 (and analogous sites on other AAV serotypes) and the N- and C-termini of AAV VP2 in AAV2 and other serotypes. In addition, chimeric viruses may be constructed combining tagged and untagged capsid proteins (e.g., an AAV capsid in which 50% of the VP3 proteins carry tag domains, and 50% of the capsid proteins do not carry a tag domain).

AAV-Polypeptide Conjugate

In an embodiment, the invention provides a conjugate comprising the inventive AAV comprising an exterior surface, which surface comprises one or more peptide tags that form a bond (a non-limiting example of which can be a covalent bond) with a binding-partner and at least one polypeptide comprising a first domain which is the binding-partner for the tag and a second domain, which is a bioactive polypeptide, wherein the AAV and the polypeptide are bound (such as, but not necessarily, covalently bound). This embodiment is schematically represented in FIG. 1, Row C. In this embodiment, the at least one polypeptide can be constructed recombinantly, employing a coding sequence in which the bioactive polypeptide-encoding domain is fused in-frame with a sequence encoding the specific binding-partner for the tag (e.g., SpyCatcher, SnoopCatcher, SpyCatcher002, and the like, as noted above).

The inventive AAV-polypeptide conjugate can incorporate any desired number of the bound bioactive polypeptides by varying the number of tags expressed on the surface of the inventive AAV by transfection of a mixture of plasmids encoding tagged and untagged capsid proteins into a packaging cell line (e.g., 293 cells). The ratio of plasmids encoding tagged vis-à-vis untagged capsid proteins, thus, can be employed to vary the number of tags on the capsid surface from 1 to 60 per capsid (there being 60 polypeptides forming the AAV capsid). For production of maximally-tagged (60 tags) AAV, no plasmids encoding untagged capsid proteins need be employed. For example, in an embodiment, the inventive AAV-polypeptide conjugate can have but one linked (a non-limiting example of which can be covalently linked) bioactive polypeptide. In other embodiments, the inventive AAV-polypeptide conjugate can have a plurality of such linked bioactive polypeptides, such as 3 or more, 5 or more, 10 or more, 20 or more (or "about" such numbers of covalently-bound bioactive molecules). The number of such linked bioactive polypeptides in the inventive AAV-polypeptide conjugate can be up to 30, or up to 50, or up to 60, depending on the desired application (or "about" such numbers of bound bioactive molecules).

Following production, the resulting AAVs can be purified and mixed (typically but not necessarily in PBS) with the polypeptides comprising a first domain which is the binding-partner for the tag and a second domain, which is a bioactive polypeptide, wherein the AAV and the polypeptide are bound (a non-limiting example of which includes being covalently bound). Purification of AAV from such packaging cell lines is routine and known to persons of ordinary skill.

The inventive AAV-polypeptide conjugate can be employed to deliver the bound bioactive polypeptide to the cell upon infection of the cell with the conjugate. This approach is particularly suited for delivery of bioactive polypeptides to cells which desirably are present transiently within the cells. This is in contrast to the typical delivery of polypeptides to cells using AAV, in which polypeptides are delivered to cells by including the gene (coding sequence) encoding the desired polypeptide as a transgene within the AAV vector genome. After infection, the AAV vector genome is retained within non-dividing cells, such that the transgenes within the AAV genome are permanently expressed within the cells, especially if under the control of a constitutive promoter. However, for certain polypeptides, constitutive, permanent, production of such polypeptides is undesirable. One such example is Cas9, which is associated with the CRISPR/Cas9 system that rapidly become one of the most powerful research tools available. In vivo delivery remains the largest obstacle to the success of CRISPR/Cas9-based approaches. Long-term overexpression of Cas9 substantially increases the risk of off-target cutting at unintended genomic sites. Therefore, an important goal for gene editing approaches is to provide efficient delivery of Cas9 transiently. The present invention, by providing AAV-polypeptide conjugates, can deliver Cas9 polypeptide to cells, rather than a permanently-expressed transgene, thus satisfying both of these challenges. Delivering Cas9 in protein form, linked to the AAV surface, provides transient activity, and frees space in the AAV genome for transgenes (such as donor DNA for the CRISPR/Cas9-based approaches, genes encoding fluorescent markers, or other desired transgenes). Because Cas9 is not genetically encoded, the protein delivered via the inventive conjugate will be degraded by the cell over time, decreasing potentially harmful long-term off-target effects.

The bioactive polypeptide domain also can be a fluorescent polypeptide, such as Green Fluorescent Peptide (GFP), such that delivery of the conjugate to the cell can facilitate tracking of infection. This is depicted, for example, in FIG. 4, Panel C.

The bioactive polypeptide domain can also be a polypeptide such as the beta subunit of Cholera toxin (CTB), or the rabies virus G protein (RVGP), the expression of which would shift the tropism of the virus. For example, and without wishing to be bound by theory, attaching CTB and RVGP to the surface of the capsid may permit it to infect peripheral nerves more efficiently and/or may improve retrograde transport.

First-AAV-Second-AAV Conjugate

In an embodiment, the invention provides a conjugate comprising the inventive AAV comprising an exterior surface, which surface comprises one or more peptide tags that form a bond (a non-limiting example being a covalent bond) with a binding-partner ("first AAV") and at least one second AAV, which second AAV comprises a second exterior surface, which second exterior surface comprises at least one binding-partner for the tag or for a separate linker molecule. Within the conjugate, the at least one first AAV and the at least one second AAV are bound. Also, as with the first AAV (as discussed above), the at least one second AAV within the conjugate preferably is a live virus.

In this embodiment (first-AAV-second-AAV conjugate), the second AAV can express the binding-partner on the second surface in the same manner as the first AAV expresses the tag (e.g., incorporated into a mutant VP2 polypeptide or other surface polypeptide).

In this embodiment (first-AAV-second-AAV conjugate), the first and second AAV can both express binding partner tags (such as SpyTag and SnoopTag) which are then bound together via a separate linker molecule (such as a SpyCatcher-SnoopCatcher fusion protein) forming a three-piece conglomerate. Other linker sequences can be employed at the SpyTag/SpyCatcher insertion sites, such as LA . . . A linkers for SpyTag/SnoopTag/SpyTag002, and for VP2 stiff linkers, long flexible linkers, and shorter linkers. FIG. 1, Row A, depicts an embodiment in which the AAVs within the conjugate are bound directly through a peptide tag/protein binding-partner interaction between the separate AAVs within the conjugate. FIG. 1, Row B depicts an embodiment in which the AAVs are bound via a third linker molecule, where the third linker molecule bridges the AAV vectors together.

The inventive first-AAV-second-AAV conjugate can incorporate any desired number of AAVs by varying the number of tags and binding-partners expressed on the surface of the first and second AAVs, by varying the ratio of capsid proteins expressing the tag in the packaging cell line, as discussed above. Thereafter, first-AAV-second-AAV conjugate can be purified, for example, based on size exclusion affinity, ion exchange FPLC chromatography, or other method that can purify conjugates having a desired number of AAVs (e.g., dimers as opposed to monomers or trimers, etc.). For example, in an embodiment, the conjugate can comprise a dimer of AAVs (see, e.g., FIG. 1, Row A). In other embodiments, the first-AAV-second-AAV conjugate can be a trimer, quadramer, pentamer, decamer, etc. Accordingly, the first-AAV-second-AAV conjugate can comprise more than one of the first AAVs (comprising the tag), more than one of the second AAVs (comprising the specific binding-partner for the tag), or both. The practical limit to the number of AAVs within the first-AAV-second-AAV conjugate is physical size, as the AAVs within the conjugate need to be able to infect cells and enter the nucleus of such cells.

One use of the inventive first-AAV-second-AAV conjugate is to effectively deliver larger transgenes than the 4.7 kB limit of a single AAV vector. Accordingly, a preferred configuration of this embodiment involves the AAVs within the conjugate comprising genomes comprising separate respective segments of a transgene, such that the complete transgene can be assembled upon infection of a cell with the first-AAV-second-AAV conjugate.

For example, treatment of many diseases, for which AAVs can be effectively used for gene therapy, require the delivery of large genes, exceeding the 4.7 kB limit of a single AAV vector. Increasing the capacity of AAV vectors while maintaining their efficiency and stability of expression is a primary goal in the field of gene therapy. One promising approach to delivering large genes is to divide the open reading frame into multiple vectors, which recombine through homologous recombination following viral infection of a cell with both (or multiple) vectors. However, it is highly unlikely for equal ratios of separate portions of a large gene to be delivered to the same cell, in the same ratio, using separate viruses. This causes a decrease in the efficiency of protein expression, and the formation of truncated protein products. This aspect of the present invention (first-AAV-second-AAV conjugate), by which AAV vectors are linked together within a conjugate, ensures high (near 100%) efficiency of co-delivery, effectively doubling (or tripling, quadrupling, etc., depending on the number of AAVs within the conjugate) the carrying capacity of an infectious unit.

The first-AAV-second-AAV conjugate can be used to deliver large genes split into multiple AAV capsids for treatment of diseases such as Stargardt's (ABCA4 as the transgene), Neurofibromatosis (NF1 as the transgene), Hemophilia, Leber's Congenital Amaurosis (CEP290 as the transgene), Duchenne muscular dystrophy, cystic fibrosis, Usher Syndrome Types I, II and III, etc. The approach also can be used to deliver multiple genes to a cell, the products of which may interact or complement each other within the cell. For example, the approach can be used to deliver both RdCVF and RdCVFL, in order to benefit from both the cone survival attributes of RdCVF and the antioxidant properties of RdCVFL (for example as in Byrne et al, Viral-mediated RdCVF and RdCVFL expression protects cone and rod photoreceptors in retinal degeneration J Clin Invest (2015) (incorporated herein in its entirely by reference)), a trophic factor and a replacement gene, such as PDE6B and XIAP (Yae et al., Caspase Inhibition with XIAP as an Adjunct to AAV Vector Gene-Replacement Therapy: Improving Efficacy and Prolonging the Treatment Window PLOS ONE (2012) (incorporated herein in its entirely by reference), or a therapeutic gene and a reporter gene, allowing a better analysis of the pattern of infectivity of therapeutic treatment, delivery of two complementary nickases based on Cas9 for increased specificity and efficiency of genome editing, etc. For example, the approach can be employed efficient functional rescue of vision by co-delivery of trophic factors and replacement genes. The approach also could be employed to link two serotypes of AAV to expand tropism of the vector.

It will be observed that the surface of the inventive AAV can have either or both of a tag (including a plurality of types of tags) or the specific binding-partner for a tag (including a plurality of tags) or both one or more tags and one or more specific binding-partners. Thus, within a conjugate comprising the first and the second AAVs, one or more of the first AAV also can comprise at least one binding-partner for the peptide tag that form a bond with a binding-partner. Similarly, within such conjugates, the second exterior surface of the at least one second AAV can comprise one or more peptide tags that form a bond with a binding-partner. It will be observed that this can facilitate multimerization of AAVs within such conjugates. See FIG. 1, Row D.

Furthermore, the inventive first-AAV-second-AAV conjugate (FIG. 1, Rows A and B) and the inventive AAV-bioactive polypeptide conjugate (FIG. 1, Row C) approaches can be employed together. In this sense, the invention permits any string of DNA-containing viral particles and proteins to be delivered together to a cell, or populations of cells, as a multimeric conjugate unit.

It will be observed that the inventive AAVs and conjugates are used to infect cells, thereby delivering transgenes and/or the linked (such as, but not limited to, covalently-linked) bioactive polypeptides to such cells. Thus, the invention provides a method of delivering a transgene to a cell by infecting the cell with one or more of the inventive AAVs or conjugates to a cell, wherein the AAV or conjugate comprises one or more transgenes. As noted, for large (larger than 4.7 kB) transgenes, a first-AAV-second-AAV conjugate can be employed to infect the cell, whereby the transgene is divided between at least two of the AAVs making up the first-AAV-second-AAV conjugate. Within the cell, these sections of the transgene then can reassemble to produce the full coding sequence for the transgene.

Similarly, the invention provides a method for delivering a bioactive polypeptide to a cell by infecting the cell with one or more of the inventive AAV-bioactive polypeptide conjugates described herein. Upon infection, the bioactive polypeptide linked (such as, but not limited to, covalently-linked) to the tag on the exterior surface of the AAV within the conjugate is delivered to the cell transiently, rather than as the product of a transgene that will be permanently expressed. As noted this is preferred for bioactive proteins, such as Cas9, to prevent off-target effects of the protein within the cell.

The inventive methods can be employed to infect any cell that AAV exhibits tropism, which is known to persons of ordinary skill. For example, the cells can be such as exocrine secretory cells (e.g., glandular cells, such as salivary gland cells, mammary gland cells, sweat gland cells, digestive gland cells, etc.), hormone secreting gland cells (e.g., pituitary cells, thyroid cells, parathyroid cells, adrenal cells, etc.), ectoderm-derived cells (e.g., keratinizing epithelial cells (e.g., making up the skin and hair), wet stratified barrier epithelial cells (e.g., of the cornea, tongue, oral cavity, gastrointestinal tract, urethra, vagina, etc.), cells of the nervous system (e.g., peripheral and central neurons, glia, etc.)), mesoderm-derived cells, cells of many internal organs (such as kidney, liver, pancreas, heart, lung) bone marrow cells, and cancerous cells either within tumors or otherwise. Preferred, and non-limiting examples of cells suitable for infection by the inventive AAVs and conjugates include, but are not limited to neurons in the peripheral and central nervous system, photoreceptors, retinal ganglion cells, retinal pigment epithelial cells, cochlear cells, Müller glia, retinal bipolar cells, amacrine cells, and horizontal cells. The cell can be in vitro or in vivo, and can be from any desired mammalian host, such as laboratory animal (rat, mouse, etc.), animal of agricultural or veterinary interest (e.g., bovine, canine, caprine, equine, feline, ovine, porcine, etc.) or primate, such as a monkey, great ape, or, preferably, a human, including a cell within a human patient.

Concomitantly, the invention provides a composition comprising a cell and one or more of the AAVs, AAV-bioactive conjugates, or AAV-AAV conjugates, as described above, wherein the cell is infected with the AAV or conjugate. The cell can be in vivo or in vitro, and any desired type for which the AAV or conjugate exhibits tropism and infectivity, as described above. Of course, wherein the cell is in vitro, the composition also includes suitable culture medium to maintain and proliferate the infected cells within the composition. Such culture media are known to persons of ordinary skill in the art, and a suitable medium can be selected depending on the type of cell within the composition.

To facilitate use in vivo, particularly a human patient, the invention also provides a pharmaceutical composition comprising one or more of the AAVs, AAV-polypeptide conjugates, or AAV-AAV conjugates, as described above and a carrier, preferably a physiologically-acceptable carrier. The carrier of the composition can be any suitable carrier for the vector. The carrier typically will be liquid, but also can be solid, or a combination of liquid and solid components. The carrier desirably is a pharmaceutically acceptable (e.g., physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood or other tissue of the intended recipient, and aqueous and non-aqueous sterile suspensions that can include suspending agents, solubilizers, thickening agents, stabilizers, and preservatives. Typically, such carriers are physiological saline solutions, which facilitate administration via skin prick, or via subdermal, intramuscular, intratumoral or parenteral injection or direct injection into whatever tissue or organ is desired. However, other carriers (e.g., salves, creams, patches, and the like, for example for transdermal administration) also can be used.

The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to up-regulate the body's natural defenses against disease. Antibiotics, i.e., microbicides and fungicides, can be present to reduce the risk of infection associated with gene transfer procedures and other disorders.

The following examples further illustrate the invention but, of course, should not be construed as in any way limiting its scope. The following methods were employed in the experiments underlying Examples 1 through 4.

Cloning and Preparation of Plasmids for Packaging

In order to produce AAV vectors incorporating SpyTag/SnoopTag, SpyCatcher, SnoopCatcher, SpyTag002, or SnoopTag002, linker peptides were engineered onto surface exposed regions of AAV capsid by PCR amplifying the insert regions and annealing with Gibson Assembly (New England Biolabs). Linker peptides were inserted into position 453 or 588 of VP3 subunit and N or C terminal of VP2 subunit of AAV. (See the Appendix for sequences).

Production of Viral Vectors

AAV vectors carrying genomes encoding GFP or mCherry and carrying SpyTag or SnoopTag on capsid proteins were produced by the plasmid co-transfection method (Grieger et. al., Production and characterization of adeno-associated viral vectors. Nat Protoc. 2006; 1(3):1412-28 (incorporated herein in its entirety by reference)) using three or four plasmids. Recombinant AAV was purified by iodixanol gradient ultracentrifugation followed by a buffer exchange and concentration with Amicon Ultra-15 Centrifugal Filter Units in PBS+0.001% Pluronic F-68. Titers were determined by quantitative PCR relative to a standard curve (Aurnhammer et al, *Hum. Gene Ther. Methods.* 23(1):18-28 (2012) (incorporated herein in its entirety by reference)).

Western Blot

SpyCatcher protein was fused with Green Fluorescent Protein (GFP), with Cas9 protein, or with beta subunit of cholera toxin by mutating the start or stop codon of the protein's coding sequence, and through Gibson cloning, inserting the coding sequence for SpyCatcher in frame at the N- or C-terminus of the protein. Protein was expressed in bacterial cells and purified. AAV-SpyTag vectors were mixed with 10 μg of GFP-SpyCatcher or 10 μg of Cas9-SpyCatcher proteins. AAV-SnoopTag vectors were mixed with 43.5 μg of SpyCatcher/SnoopCatcher fusion protein linker molecule. In order to link AAV-vectors together, AAV-SnoopTag and AAV-SpyTag vectors were mixed with Spycatcher/SnoopCatcher fusion protein linker molecule. These were incubated at RT for 1 hour, followed by overnight at 4° C.

The mixture was run on a 6-8% Tris-Glycine gel the following day. Protein was transferred to a PVDF membrane, and blocked in 5% milk for 1 hour. The membrane was then washed 3×5 minutes in TBST, and incubated in primary antibodies overnight at 4° C.: Mouse monoclonal antibody against VP1, 2 and 3 from Progen (1:100). The membrane was washed in TBST for 15 minutes followed by 4×5 minutes. Anti-mouse secondary antibody (Li-Cor, 1:2000) was applied for 1 hour at RT before washing and visualization using Odyssey CLx Imaging System (Li-cor).

CRISPR/Cas9 Transfection

The Cas9-SpyCatcher fusion protein was tested for its editing ability. Four different gRNAs were designed targeting the human Rhodopsin gene and synthesized using GeneArt Precision gRNA Synthesis Kit (Thermo Fisher Scientific). Cas9-SpyCatcher, together with gRNAs were transfected into HEK293 cells by using Lipofectamine CRISPRMAX Transfection Reagent (Thermo Fisher Scientific). Concentrations of Cas9-SpyCatcher and gRNA were determined according to Lipofectamine CRISPRMAX Transfection protocol. The cells were incubated for 72 hours before testing the editing efficiency.

AAV-SpyTag-Cas9-SpyCatcher-RNP Assembly

To prepare the Cas9 RNP complexes, Cas9-SpyCatcher protein was incubated with sgRNA at 2:1 or 4:1 molar ratio. In one method, Cas9-SpyCatcher protein was mixed with AAV-SpyTag vector one day prior to infecting the cells. Immediately before the experiment, sgRNA was added to the mixture and incubated at RT for 10 or 20 minutes. In another method, AAV-SpyTag vector, Cas9-SpyCatcher protein and sgRNA were mixed together and incubated for 30 minutes at RT. HEK293 cells were infected with the assembly and incubated for 72 hours before testing the editing efficiency.

Testing the CRISPR/Cas9 Editing Efficiency

To quantify the editing ability at desired genomic loci, T7 endonuclease I assays were performed on HEK293T cells, using a guide RNA UAGAGCGUGAGGAAGUUGAU (SEQ ID NO:12), which directs genome editing to the rhodopsin gene. For T7 endo-nuclease I assays, genomic DNA was extracted ~72 h post-transfection using the Qiagen DNeasy Blood and Tissue Kit. Primers (hRHO 1 Fw: AGGCCTTCGCAGCATTCTT (SEQ ID NO:13) and hRHO 1 Rv: GCAGCACCCCATCTGTTTTC (SEQ ID NO:14)) were designed to amplify a ~1 kb region containing the target site and Q5 High-Fidelity DNA Polymerase was used for amplification. The PCR reaction was purified with Zymo DNA Clean and Concentrator followed by a T7 Endonuclease 1 digestion. The samples treated with T7 Endonuclease were run on an agarose gel together with undigested samples.

Example 1

This example demonstrates the generation, stability, and infectivity of an AAV comprising an exterior surface, which surface comprises one or more peptide tags that form a covalent bond with a binding-partner, wherein the AAV is a live virus.

Linker peptides (tags) SpyTag and SnoopTag, and the specific binding-partner, SnoopCatcher, were engineered into surface exposed regions of the AAV capsid, including position 453, 588 of VP3 and the C or N terminus of VP2 subunit.

Titering of viruses, performed using QPCR (as in Aurnhammer et al. Universal real-time PCR for the detection and quantification of adeno-associated virus serotype 2-derived inverted terminal repeat sequences. *Hum. Gene. Ther. Methods.* 23(1):18-28 (2012) (incorporated herein in its entirety by reference)) carrying linker molecules demonstrated that the inventive AAV can carry these linkers (tags and specific binding-partners) without affecting viral stability and infectivity. This is presented in Table 1.

TABLE 1

High viral titers from iodixanol-purified virus demonstrate stability of AAV capsids after insertion of linker molecules on surface-exposed regions in VP2 and VP3. "TG_GLS" indicates that TG and GLS sequences were included to flank the N- and C- ends of the SpyTag insert (e.g., TG-SpyTag-GLS), to provide flexibility and allow for efficient viral packaging.

| Linker molecule | AAV serotype | Position | Linker Sequences | Titer |
|---|---|---|---|---|
| SpyTag | AAV2 | VP3~453 | TG_GLS | 7.92E+12 vg/mL |
| SpyTag | AAV2 | VP3~453 | No linker | 2.9E+13 vg/mL |
| SpyTag | AAV2 | VP3~588 | TG_GLS | 6.54E+13 vg/mL |
| SnoopTag | AAV2 | VP3~588 | TG_GLS | 1.24E+14 vg/mL |
| SpyTag | 7m8 (AAV2-based) | VP3~453 | No linker | 5.4E+13 vg/mL |
| SpyTag | 7m8 (AAV2-based) | C terminus of VP2 | GSGGSGGSG | 4.82E+14 vg/mL |
| SnoopTag | 7m8 (AAV2-based) | C terminus of VP2 | GSGGSGGSG | 3.91E+13 vg/mL |
| SpyTag | AAV2/AAV2-SpyTag chimera (5:1 ratio, VP3:VP3-SpyTag) | VP3~453 | TG_GLS | 4.5E+13 vg/mL |

Example 2

This example demonstrates the generation of a First AAV-Second AAV conjugate as described herein.

The AAV species referenced in Example 1 were mixed together and observed by electron microscopy. As depicted in FIG. 2, paired AAV viral conjugates were visible. FIG. 2, Panel A: AAV2 vectors as control. FIG. 2, Panel B: AAV2-SpyTag vectors linked with AAV2-SnoopTag vectors, linked by a SpyCatcher/SnoopCatcher linker protein. Viruses appear as dimers or trimers. FIG. 2, Panel C: Overexpression of SpyTag/SnoopTag linkers cause the formation of a clump of AAV capsids, in which many AAV vectors are tethered together.

The ability of tag-expressing (first AAV) and binding-partner-expressing (second AAV) to form linked conjugates also was ascertained by Western blot assessment. FIG. 3 depicts these data demonstrating the linkage of SpyTag expressing and SnoopTag-expressing AAV capsids, bound via a linker molecule made of SpyCatcher-SnoopCatcher fusion protein.

Example 3

This example demonstrates the generation of an AAV-Polypeptide Conjugate as described herein.

The AAV2-SpyTag was bound to a polypeptide in which Green Fluorescent Protein (GFP or mClover) was linked to SpyCatcher (GFP-SpyCatcher) (FIG. 4, Panel A). GFP-bound viral particles were tracked by super resolution microscopy in 293 cells. The results showed that the viral particle is infectious and that the linked protein is functional (FIG. 4, Panel C).

Example 4

This example demonstrates the generation of an AAV-Polypeptide Conjugate as described herein.

Cas9 was fused to SpyCatcher to enable its binding to AAV-SpyTag vectors. First, the cutting efficiency of Cas9-SpyCatcher fusion protein with a guide RNA targeting human Rhodopsin was studied in HEK293T cells. The results are presented in FIG. 5, Panel A, and they reveal that the Cas9-SpyCatcher polypeptide delivered by infection of the AAV-Cas9-SpyCatcher conjugate successfully cleaved the target (Rhodopsin).

The binding ability of Cas9-SpyCatcher to AAV2-SpyTag also was assessed by Western blot analysis. The results are presented in FIG. 5, Panel B. The results demonstrate binding of AAV2-SpyTag to Cas9-SpyCatcher.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

APPENDIX

SEQUENCES

SEQ ID NO: 1: Part of sequence including the insert (underlined) of AAV2-588-SPYTAG (with TG_GLS linkers):

```
ATGGCTGCCGATGGTTATCTTCCAGATTGGCTCGAGGACACTCTCTCTGAAGGAATAAGACAGTGGTGGAAGCTCAAACCTGGCCCAC
CACCACCAAAGCCCGCAGAGCGGCATAAGGACGACAGCAGGGGTCTTGTGCTTCCTGGGTACAAGTACCTCGGACCCTTCAACGGACT
CGACAAGGGAGAGCCGGTCAACGAGGCAGACGCCGCGGCCCTCGAGCACGACAAAGCCTACGACCGGCAGCTCGACAGCGGAGACAAC
CCGTACCTCAAGTACAACCACGCCGACGCGGAGTTTCAGGAGCGCCTTAAAGAAGATACGTCTTTTGGGGGCAACCTCGGACGAGCAG
TCTTCCAGGCGAAAAAGAGGGTTCTTGAACCTCTGGGCCTGGTTGAGGAACCTGTTAAGACGGCTCCGGGAAAAAAGAGGCCGGTAGA
GCACTCTCCTGTGGAGCCAGACTCCTCCTCGGGAACCGGAAAGGCGGGCCAGCAGCCTGCAAGAAAAAGATTGAATTTTGGTCAGACT
GGAGACGCAGACTCAGTACCTGACCCCCAGCCTCTCGGACAGCCACCAGCAGCCCCCTCTGGTCTGGGAACTAATACGATGGCTACAG
GCAGTGGCGCACCAATGGCAGACAATAACGAGGGCGCCGACGGAGTGGGTAATTCCTCGGGAAATTGGCATTGCGATTCCACATGGAT
GGGCGACAGAGTCATCACCACCAGCACCCGAACCTGGGCCCTGCCCACCTACAACAACCACCTCTACAAACAAATTTCCAGCCAATCA
GGAGCCTCGAACGACAATCACTACTTTGGCTACAGCACCCCTTGGGGGTATTTTGACTTCAACAGATTCCACTGCCACTTTTCACCAC
GTGACTGGCAAAGACTCATCAACAACAACTGGGGATTCCGACCCAAGAGACTCAACTTCAAGCTCTTTAACATTCAAGTCAAAGAGGT
CACGCAGAATGACGGTACGACGACGATTGCCAATAACCTTACCAGCACGGTTCAGGTGTTTACTGACTCGGAGTACCAGCTCCCGTAC
GTCCTCGGCTCGGCGCATCAAGGATGCCTCCCGCCGTTCCCAGCAGACGTCTTCATGGTGCCACAGTATGGATACCTCACCCTGAACA
ACGGGAGTCAGGCAGTAGGACGCTCTTCATTTTACTGCCTGGAGTACTTTCCTTCTCAGATGCTGCGTACCGGAAACAACTTTACCTT
CAGCTACACTTTTGAGGACGTTCCTTTCCACAGCAGCTACGCTCACAGCCAGAGTCTGGACCGTCTCATGAATCCTCTCATCGACCAG
TACCTGTATTACTTGAGCAGAACAAAACACTCCAAGTGGAACCACCACGCAGTCAAGGCTTCAGTTTTCTCAGGCCGGAGCGAGTGACA
TTCGGGACCAGTCTAGGAACTGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGGCCATGGCAAGCCACAAGGAC
GATGAAGAAAAGTTTTTTCCTCAGAGCGGGGTTCTCATCTTTGGGAAGCAAGGCTCAGAGAAAACAAATGTGGACATTGAAAAGGTCA
TGATTACAGACGAAGAGGAAATCAGGACAACCAATCCCGTGGCTACGGAGCAGTATGGTTCTGTATCTACCAGAAATCAGGACAACCA
ATCCCGTGGCTACGGAGCAGTATGGTTCTGTATCTACCAACCTCCAGAGAGGCAACACCGGTGCCCACATCGTGATGGTGGACGCCTA
CAAGCCGACGAAGGGCTTAAGTAGACAAGCAGCTACCGCAGATGTCAACACACAAGGCGTTCTTCCAGGCATGGTCTGGCAGGACAGA
GATGTGTACCTTCAGGGGCCCATCTGGGCAAAGATTCCACACACGGACGGACATTTTCACCCCTCTCCCCTCATGGGTGGATTCGGAC
TTAAACACCCTCCTCCACAGATTCTCATCAAGAACACCCCGGTACCTGCGAATCCTTCGACCACCTTCAGTGCGGCAAAGTTTGCTTC
CTTCATCACACAGTACTCCACGGGACAGGTCAGCGTGGAGATCGAGTGGGAGCTGCAGAAGGAAAACAGCAAACGCTGGAATCCCGAA
ATTCAGTACACTTCCAACTACAACAAGTCTGTTAATGTGGACTTTACTGTGGACACTAATGGCGTGTATTCAGAGCCTCGCCCCATTG
GCACCAGATACCTGACTCGTAATCTGTA
```

SEQ ID NO: 2: Part of sequence including the insert (underlined) of AAV2-588-SNOOPTAG (with TG_GLS linkers):

```
ATGGCTGCCGATGGTTATCTTCCAGATTGGCTCGAGGACACTCTCTCTGAAGGAATAAGACAGTGGTGGAAGCTCAAACCTGGCCCAC
CACCACCAAAGCCCGCAGAGCGGCATAAGGACGACAGCAGGGGTCTTGTGCTTCCTGGGTACAAGTACCTCGGACCCTTCAACGGACT
CGACAAGGGAGAGCCGGTCAACGAGGCAGACGCCGCGGCCCTCGAGCACGACAAAGCCTACGACCGGCAGCTCGACAGCGGAGACAAC
CCGTACCTCAAGTACAACCACGCCGACGCGGAGTTTCAGGAGCGCCTTAAAGAAGATACGTCTTTTGGGGGCAACCTCGGACGAGCAG
TCTTCCAGGCGAAAAAGAGGGTTCTTGAACCTCTGGGCCTGGTTGAGGAACCTGTTAAGACGGCTCCGGGAAAAAAGAGGCCGGTAGA
GCACTCTCCTGTGGAGCCAGACTCCTCCTCGGGAACCGGAAAGGCGGGCCAGCAGCCTGCAAGAAAAAGATTGAATTTTGGTCAGACT
GGAGACGCAGACTCAGTACCTGACCCCCAGCCTCTCGGACAGCCACCAGCAGCCCCCTCTGGTCTGGGAACTAATACGATGGCTACAG
GCAGTGGCGCACCAATGGCAGACAATAACGAGGGCGCCGACGGAGTGGGTAATTCCTCGGGAAATTGGCATTGCGATTCCACATGGAT
GGGCGACAGAGTCATCACCACCAGCACCCGAACCTGGGCCCTGCCCACCTACAACAACCACCTCTACAAACAAATTTCCAGCCAATCA
```

APPENDIX-continued

SEQUENCES

GGAGCCTCGAACGACAATCACTACTTTGGCTACAGCACCCCTTGGGGGTATTTTGACTTCAACAGATTCCACTGCCACTTTTCACCAC
GTGACTGGCAAAGACTCATCAACAACAACTGGGGATTCCGACCCAAGAGACTCAACTTCAAGCTCTTTAACATTCAAGTCAAAGAGGT
CACGCAGAATGACGGTACGACGACGATTGCCAATAACCTTACCAGCACGGTTCAGGTGTTTACTGACTCGGAGTACCAGCTCCCGTAC
GTCCTCGGCTCGGCGCATCAAGGATGCCTCCCGCCGTTCCCAGCAGACGTCTTCATGGTGCCACAGTATGGATACCTCACCCTGAACA
ACGGGAGTCAGGCAGTAGGACGCTCTTCATTTTACTGCCTGGAGTACTTTCCTTCTCAGATGCTGCGTACCGGAAACAACTTTACCTT
CAGCTACACTTTTGAGGACGTTCCTTTCCACAGCAGCTACGCTCACAGCCAGAGTCTGGACCGTCTCATGAATCCTCTCATCGACCAG
TACCTGTATTACTTGAGCAGAACAAACACTCCAAGTGGAACCACCACGCAGTCAAGGCTTCAGTTTTCTCAGGCCGGAGCGAGTGACA
TTCGGGACCAGTCTAGGAACTGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGGCCATGGCAAGCCACAAGGAC
GATGAAGAAAAGTTTTTTCCTCAGAGCGGGGTTCTCATCTTTGGGAAGCAAGGCTCAGAGAAAACAAATGTGGACATTGAAAAGGTCA
TGATTACAGACGAAGAGGAAATCAGGACAACCAATCCCGTGGCTACGGAGCAGTATGGTTCTGTATCTACCAACCTCCAGAGAGGCAA
CACCGGTAAACTGGGCGACATAGAGTTTATCAAGGTGAACAAAGGCTTAAGTAGACAAGCAGCTACCGCAGATGTCAACACACAAGGC
GTTCTTCCAGGCATGGTCTGGCAGGACAGAGATGTGTACCTTCAGGGGCCCATCTGGGCAAAGATTCCACACACGGACGGACATTTTC
ACCCCTCTCCCCTCATGGGTGGATTCGGACTTAAACACCCTCCTCCACAGATTCTCATCAAGAACACCCCGGTACCTGCGAATCCTTC
GACCACCTTCAGTGCGGCAAAGTTTGCTTCCTTCATCACACAGTACTCCACGGGACAGGTCAGCGTGGAGATCGAGTGGGAGCTGCAG
AAGGAAAACAGCAAACGCTGGAATCCCGAAATTCAGTACACTTCCAACTACAACAAGTCTGTTAATGTGGACTTTACTGTGGACACTA
ATGGCGTGTATTCAGAGCCTCGCCCCATTGGCACCAGATACCTGACTCGTAATCTGTA

SEQ ID NO: 3: Part of sequence including the insert (underlined) of AAV2-453-SPYTAG
(no linkers):
ATGGCTGCCGATGGTTATCTTCCAGATTGGCTCGAGGACACTCTCTCTGAAGGAATAAGACAGTGGTGGAAGCTCAAACCTGGCCCAC
CACCACCAAAGCCCGCAGAGCGGCATAAGGACGACAGCAGGGGTCTTGTGCTTCCTGGGTACAAGTACCTCGGACCCTTCAACGGACT
CGACAAGGGAGAGCCGGTCAACGAGGCAGACGCCGCGGCCCTCGAGCACGACAAAGCCTACGACCGGCAGCTCGACAGCGGAGACAAC
CCGTACCTCAAGTACAACCACGCCGACGCGGAGTTTCAGGAGCGCCTTAAAGAAGATACGTCTTTTGGGGGCAACCTCGGACGAGCAG
TCTTCCAGGCGAAAAGAGGGGTTCTTGAACCTCTGGGCCTGGTTGAGGAACCTGTTAAGACGGCTCCGGGAAAAAAGAGGCCGGTAGA
GCACTCTCCTGTGGAGCCAGACTCCTCCTCGGGAACCGGAAAGGCGGGCCAGCAGCCTGCAAGAAAAAGATTGAATTTTGGTCAGACT
GGAGACGCAGACTCAGTACCTGACCCCCAGCCTCTCGGACAGCCACCAGCAGCCCCTCTGGTCTGGGAACTAATACGATGGCTACAG
GCAGTGGCGCACCAATGGCAGACAATAACGAGGGCGCCGACGGAGTGGGTAATTCCTCGGGAAATTGGCATTGCGATTCCACATGGAT
GGGCGACAGAGTCATCACCACCAGCACCCGAACCTGGGCCCTGCCCACCTACAACAACCACCTCTACAAACAAATTTCCAGCCAATCA
GGAGCCTCGAACGACAATCACTACTTTGGCTACAGCACCCCTTGGGGGTATTTTGACTTCAACAGATTCCACTGCCACTTTTCACCAC
GTGACTGGCAAAGACTCATCAACAACAACTGGGGATTCCGACCCAAGAGACTCAACTTCAAGCTCTTTAACATTCAAGTCAAAGAGGT
CACGCAGAATGACGGTACGACGACGATTGCCAATAACCTTACCAGCACGGTTCAGGTGTTTACTGACTCGGAGTACCAGCTCCCGTAC
GTCCTCGGCTCGGCGCATCAAGGATGCCTCCCGCCGTTCCCAGCAGACGTCTTCATGGTGCCACAGTATGGATACCTCACCCTGAACA
ACGGGAGTCAGGCAGTAGGACGCTCTTCATTTTACTGCCTGGAGTACTTTCCTTCTCAGATGCTGCGTACCGGAAACAACTTTACCTT
CAGCTACACTTTTGAGGACGTTCCTTTCCACAGCAGCTACGCTCACAGCCAGAGTCTGGACCGTCTCATGAATCCTCTCATCGACCAG
TACCTGTATTACTTGAGCAGAACAAACACTCCAAGTGGAGCCCACATCGTGATGGTGGACGCCTACAAGCCGACGAAGACCACCACGC
AGTCAAGGCTTCAGTTTTCTCAGGCCGGAGCGAGTGACATTCGGGACCAGTCTAGGAACTGGCTTCCTGGACCCTGTTACCGCCAGCA
GCGAGTATCAAAGACATCTGCGGATAACAACAACAGTGAATACTCGTGGACTGGAGCTACCAAGTACCACCTCAATGGCAGAGACTCT
CTGGTGAATCCGGGCCCGGCCATGGCAAGCCACAAGGACGATGAAGAAAAGTTTTTTCCTCAGAGCGGGGTTCTCATCTTTGGGAAGC
AAGGCTCAGAGAAAACAAATGTGGACATTGAAAAGGTCATGATTACAGACGAAGAGGAAATCAGGACAACCAATCCCGTGGCTACGGA
GCAGTATGGTTCTGTATCTACCAACCTCCAGAGAGGCAACAGACAAGCAGCTACCGCAGATGTCAACACACAAGGCGTTCTTCCAGGC
ATGGTCTGGCAGGACAGAGATGTGTACCTTCAGGGGCCCATCTGGGCAAAGATTCCACACACGGACGGACATTTTCACCCCTCTCCCC
TCATGGGTGGATTCGGACTTAAACACCCTCCTCCACAGATTCTCATCAAGAACACCCCGGTACCTGCGAATCCTTCGACCACCTTCAG
TGCGGCAAAGTTTGCTTCCTTCATCACACAGTACTCCACGGGACAGGTCAGCGTGGAGATCGAGTGGGAGCTGCAGAAGGAAAACAGC
AAACGCTGGAATCCCGAAATTCAGTACACTTCCAACTACAACAAGTCTGTTAATGTGGACTTTACTGTGGACACTAATGGCGTGTATT
CAGAGCCTCGCCCCATTGGCACCAGATACCTGACTCGTAATCTGTA SEQ ID NO: 4: Part of sequence including the insert (underlined) of AAV2-453-SPYTAG
(with TG_GLS linkers):
ATGGCTGCCGATGGTTATCTTCCAGATTGGCTCGAGGACACTCTCTCTGAAGGAATAAGACAGTGGTGGAAGCTCAAACCTGGCCCAC
CACCACCAAAGCCCGCAGAGCGGCATAAGGACGACAGCAGGGGTCTTGTGCTTCCTGGGTACAAGTACCTCGGACCCTTCAACGGACT
CGACAAGGGAGAGCCGGTCAACGAGGCAGACGCCGCGGCCCTCGAGCACGACAAAGCCTACGACCGGCAGCTCGACAGCGGAGACAAC
CCGTACCTCAAGTACAACCACGCCGACGCGGAGTTTCAGGAGCGCCTTAAAGAAGATACGTCTTTTGGGGGCAACCTCGGACGAGCAG
TCTTCCAGGCGAAAAGAGGGGTTCTTGAACCTCTGGGCCTGGTTGAGGAACCTGTTAAGACGGCTCCGGGAAAAAAGAGGCCGGTAGA
GCACTCTCCTGTGGAGCCAGACTCCTCCTCGGGAACCGGAAAGGCGGGCCAGCAGCCTGCAAGAAAAAGATTGAATTTTGGTCAGACT
GGAGACGCAGACTCAGTACCTGACCCCCAGCCTCTCGGACAGCCACCAGCAGCCCCTCTGGTCTGGGAACTAATACGATGGCTACAG
GCAGTGGCGCACCAATGGCAGACAATAACGAGGGCGCCGACGGAGTGGGTAATTCCTCGGGAAATTGGCATTGCGATTCCACATGGAT
GGGCGACAGAGTCATCACCACCAGCACCCGAACCTGGGCCCTGCCCACCTACAACAACCACCTCTACAAACAAATTTCCAGCCAATCA
GGAGCCTCGAACGACAATCACTACTTTGGCTACAGCACCCCTTGGGGGTATTTTGACTTCAACAGATTCCACTGCCACTTTTCACCAC
GTGACTGGCAAAGACTCATCAACAACAACTGGGGATTCCGACCCAAGAGACTCAACTTCAAGCTCTTTAACATTCAAGTCAAAGAGGT
CACGCAGAATGACGGTACGACGACGATTGCCAATAACCTTACCAGCACGGTTCAGGTGTTTACTGACTCGGAGTACCAGCTCCCGTAC
GTCCTCGGCTCGGCGCATCAAGGATGCCTCCCGCCGTTCCCAGCAGACGTCTTCATGGTGCCACAGTATGGATACCTCACCCTGAACA
ACGGGAGTCAGGCAGTAGGACGCTCTTCATTTTACTGCCTGGAGTACTTTCCTTCTCAGATGCTGCGTACCGGAAACAACTTTACCTT
CAGCTACACTTTTGAGGACGTTCCTTTCCACAGCAGCTACGCTCACAGCCAGAGTCTGGACCGTCTCATGAATCCTCTCATCGACCAG
TACCTGTATTACTTGAGCAGAACAAACACTCCAAGTGGA**ACCGGTCCACATCGTGATGGTGGACGCCTACAAGCCGACGAAGGGCT
TAAGT**ACCACCACGCAGTCAAGGCTTCAGTTTTCTCAGGCCGGAGCGAGTGACATTCGGGACCAGTCTAGGAACTGGCTTCCTGGACC
CTGTTACCGCCAGCAGCGAGTATCAAAGACATCTGCGGATAACAACAACAGTGAATACTCGTGGACTGGAGCTACCAAGTACCACCTC
AATGGCAGAGACTCTCTGGTGAATCCGGGCCCGGCCATGGCAAGCCACAAGGACGATGAAGAAAAGTTTTTTCCTCAGAGCGGGGTTC
TCATCTTTGGGAAGCAAGGCTCAGAGAAAACAAATGTGGACATTGAAAAGGTCATGATTACAGACGAAGAGGAAATCAGGACAACCAA
TCCCGTGGCTACGGAGCAGTATGGTTCTGTATCTACCAACCTCCAGAGAGGCAACAGACAAGCAGCTACCGCAGATGTCAACACACAA
GGCGTTCTTCCAGGCATGGTCTGGCAGGACAGAGATGTGTACCTTCAGGGGCCCATCTGGGCAAAGATTCCACACACGGACGGACATT
TTCACCCCTCTCCCCTCATGGGTGGATTCGGACTTAAACACCCTCCTCCACAGATTCTCATCAAGAACACCCCGGTACCTGCGAATCC
TTCGACCACCTTCAGTGCGGCAAAGTTTGCTTCCTTCATCACACAGTACTCCACGGGACAGGTCAGCGTGGAGATCGAGTGGGAGCTG
CAGAAGGAAAACAGCAAACGCTGGAATCCCGAAATTCAGTACACTTCCAACTACAACAAGTCTGTTAATGTGGACTTTACTGTGGACA
CTAATGGCGTGTATTCAGAGCCTCGCCCCATTGGCACCAGATACCTGACTCGTAATCTGTA APPENDIX-continued

SEQUENCES

SEQ ID NO: 5: Part of sequence including the insert (underlined) in C terminus of
VP2-SPYTAG (with a GSGGSGGSG linker):
AGGCCGGTAGAGCACTCTCCTGTGGAGCCAGACTCCTCCTCGGGAACCGGAAAGGCGGGCCAGCAGCCTGCAAGAAAAAGATTGAATT
TTGGTCAGACTGGAGACGCAGACTCAGTACCTGACCCCCAGCCTCTCGGACAGCCACCAGCAGCCCCCTCTGGTCTGGGAACTAATAC
GATGGCTACAGGCAGTGGCGCACCAATGGCAGACAATAACGAGGGCGCCGACGGAGTGGGTAATTCCTCGGGAAATTGGCATTGCGAT
TCCACATGGATGGGCGACAGAGTCACCACCACCAGCACCCGAACCTGGGCCCTGCCCACCTACAACAACCACCTCTACAAACAAATTT
CCAGCCAATCAGGAGCCTCGAACGACAATCACTACTTTGGCTACAGCACCCCTTGGGGGTATTTTGACTTCAACAGATTCCACTGCCA
CTTTTCACCACGTGACTGGCAAAGACTCATCAACAACAACTGGGGATTCCGACCCAAGAGACTCAACTTCAAGCTCTTTAACATTCAA
GTCAAAGAGGTCACGCAGAATGACGGTACGACGACGATTGCCAATAACCTTACCAGCACGGTTCAGGTGTTTACTGACTCGGAGTACC
AGCTCCCGTACGTCCTCGGCTCGGCGCATCAAGGATGCCTCCCGCCGTTCCCAGCAGACGTCTTCATGGTGCCACAGTATGGATACCT
CACCCTGAACAACGGGAGTCAGGCAGTAGGACGCTCTTCATTTTACTGCCTGGAGTACTTTCCTTCTCAGATGCTGCGTACCGGAAAC
AACTTTACCTTCAGCTACACTTTTGAGGACGTTCCTTTCCACAGCAGCTACGCTCACAGCCAGAGTCTGGACCGTCTCATGAATCCTC
TCATCGACCAGTACCTGTATTACTTGAGCAGAACAAACACTCCAAGTGGAACCACCACGCAGTCAAGGCTTCAGTTTTCTCAGGCCGG
AGCGAGTGACATTCGGGACCAGTCTAGGAACTGGCTTCCTGGACCCTGTTACCGCCAGCAGCGAGTATCAAAGACATCTGCGGATAAC
AACAACAGTGAATACTCGTGGACTGGAGCTACCAAGTACCACCTCAATGGCAGAGACTCTCTGGTGAATCCGGGCCCGGCCATGGCAA
GCCACAAGGACGATGAAGAAAAGTTTTTTCCTCAGAGCGGGGTTCTCATCTTTGGGAAGCAAGGCTCAGAGAAAACAAATGTGGACAT
TGAAAAGGTCATGATTACAGACGAAGAGGAAATCAGGACAACCAATCCCGTGGCTACGGAGCAGTATGGTTCTGTATCTACCAACCTC
CAGAGAGGCAACAGACAAGCAGCTACCGCAGATGTCAACACACAAGGCGTTCTTCCAGGCATGGTCTGGCAGGACAGAGATGTGTACC
TTCAGGGGCCCATCTGGGCAAAGATTCCACACACGGACGGACATTTTCACCCCTCTCCCCTCATGGGTGGATTCGGACTTAAACACCC
TCCTCCACAGATTCTCATCAAGAACACCCCGGTACCTGCGAATCCTTCGACCACCTTCAGTGCGGCAAAGTTTGCTTCCTTCATCACA
CAGTACTCCACGGGACAGGTCAGCGTGGAGATCGAGTGGGAGCTGCAGAAGGAAAACAGCAAACGCTGGAATCCCGAAATTCAGTACA
CTTCCAACTACAACAAGTCTGTTAATGTGGACTTTACTGTGGACACTAATGGCGTGTATTCAGAGCCTCGCCCCATTGGCACCAGATA
CCTGACTCGTAATCTG<u>GGCAGCGGCGGCAGCGGCGGCAGCGGCGCCCACATCGTGATGGTGGACGCCTACAAGCCGACGAAG</u>

SEQ ID NO: 6: Part of sequence including the insert (underlined) in C terminus of
VP2-SNOOPTAG (with a GSGGSGGSG linker):
AGGCCGGTAGAGCACTCTCCTGTGGAGCCAGACTCCTCCTCGGGAACCGGAAAGGCGGGCCAGCAGCCTGCAAGAAAAAGATTGAATT
TTGGTCAGACTGGAGACGCAGACTCAGTACCTGACCCCCAGCCTCTCGGACAGCCACCAGCAGCCCCCTCTGGTCTGGGAACTAATAC
GATGGCTACAGGCAGTGGCGCACCAATGGCAGACAATAACGAGGGCGCCGACGGAGTGGGTAATTCCTCGGGAAATTGGCATTGCGAT
TCCACATGGATGGGCGACAGAGTCACCACCACCAGCACCCGAACCTGGGCCCTGCCCACCTACAACAACCACCTCTACAAACAAATTT
CCAGCCAATCAGGAGCCTCGAACGACAATCACTACTTTGGCTACAGCACCCCTTGGGGGTATTTTGACTTCAACAGATTCCACTGCCA
CTTTTCACCACGTGACTGGCAAAGACTCATCAACAACAACTGGGGATTCCGACCCAAGAGACTCAACTTCAAGCTCTTTAACATTCAA
GTCAAAGAGGTCACGCAGAATGACGGTACGACGACGATTGCCAATAACCTTACCAGCACGGTTCAGGTGTTTACTGACTCGGAGTACC
AGCTCCCGTACGTCCTCGGCTCGGCGCATCAAGGATGCCTCCCGCCGTTCCCAGCAGACGTCTTCATGGTGCCACAGTATGGATACCT
CACCCTGAACAACGGGAGTCAGGCAGTAGGACGCTCTTCATTTTACTGCCTGGAGTACTTTCCTTCTCAGATGCTGCGTACCGGAAAC
AACTTTACCTTCAGCTACACTTTTGAGGACGTTCCTTTCCACAGCAGCTACGCTCACAGCCAGAGTCTGGACCGTCTCATGAATCCTC
TCATCGACCAGTACCTGTATTACTTGAGCAGAACAAACACTCCAAGTGGAACCACCACGCAGTCAAGGCTTCAGTTTTCTCAGGCCGG
AGCGAGTGACATTCGGGACCAGTCTAGGAACTGGCTTCCTGGACCCTGTTACCGCCAGCAGCGAGTATCAAAGACATCTGCGGATAAC
AACAACAGTGAATACTCGTGGACTGGAGCTACCAAGTACCACCTCAATGGCAGAGACTCTCTGGTGAATCCGGGCCCGGCCATGGCAA
GCCACAAGGACGATGAAGAAAAGTTTTTTCCTCAGAGCGGGGTTCTCATCTTTGGGAAGCAAGGCTCAGAGAAAACAAATGTGGACAT
TGAAAAGGTCATGATTACAGACGAAGAGGAAATCAGGACAACCAATCCCGTGGCTACGGAGCAGTATGGTTCTGTATCTACCAACCTC
CAGAGAGGCAACAGACAAGCAGCTACCGCAGATGTCAACACACAAGGCGTTCTTCCAGGCATGGTCTGGCAGGACAGAGATGTGTACC
TTCAGGGGCCCATCTGGGCAAAGATTCCACACACGGACGGACATTTTCACCCCTCTCCCCTCATGGGTGGATTCGGACTTAAACACCC
TCCTCCACAGATTCTCATCAAGAACACCCCGGTACCTGCGAATCCTTCGACCACCTTCAGTGCGGCAAAGTTTGCTTCCTTCATCACA
CAGTACTCCACGGGACAGGTCAGCGTGGAGATCGAGTGGGAGCTGCAGAAGGAAAACAGCAAACGCTGGAATCCCGAAATTCAGTACA
CTTCCAACTACAACAAGTCTGTTAATGTGGACTTTACTGTGGACACTAATGGCGTGTATTCAGAGCCTCGCCCCATTGGCACCAGATA
CCTGACTCGTAATCTG<u>GGCAGCGGCGGCAGCGGCGGCAGCGGCAAACTGGGCGACATAGAGTTTATCAAGGTGAACAAA</u>

SEQ ID NO: 7: Part of sequence including the insert (underlined) of AAV2-588-SPYTAG002
(with TG_GLS linkers):
ATGGCTGCCGATGGTTATCTTCCAGATTGGCTCGAGGACACTCTCTCTGAAGGAATAAGACAGTGGTGGAAGCTCAAACCTGGCCCAC
CACCACCAAAGCCCGCAGAGCGGCATAAGGACGACAGCAGGGGTCTTGCTTCCTGGGTACAAGTACCTCGGACCCTTCAGCGGACT
CGACAAGGGAGAGCCGGTCAACGAGGCAGACGCCGCGGCCCTCGAGCACGACAAAGCCTACGACCGGCAGCTCGACAGCGGAGACAAC
CCGTACCTCAAGTACAACCACGCCGACGCGGAGTTTCAGGAGCGCCTTAAAGAAGATACGTCTTTTGGGGGCAACCTCGGACGAGCAG
TCTTCCAGGCGAAAAGAGGGGTTCTTGAACCTCTGGGCCTGGTTGAGGAACCTGTTAAGACGGCTCCGGGAAAAAAGAGGCCGGTAGA
GCACTCTCCTGTGGAGCCAGACTCCTCCTCGGGAACCGGAAAGGCGGGCCAGCAGCCTGCAAGAAAAAGATTGAATTTGGTCAGACT
GGAGACGCAGACTCAGTACCTGACCCCCAGCCTCTCGGACAGCCACCAGCAGCCCCCTCTGGTCTGGGAACTAATACGATGGCTACAG
GCAGTGGCGCACCAATGGCAGACAATAACGAGGGCGCCGACGGAGTGGGTAATTCCTCGGGAAATTGGCATTGCGATTCCACATGGAT
GGGCGACAGAGTCATCACCACCAGCACCCGAACCTGGGCCCTGCCCACCTACAACAACCACCTCTACAAACAAATTTCCAGCCAATCA
GGAGCCTCGAACGACAATCACTACTTTGGCTACAGCACCCCTTGGGGTATTTTGACTTCAACAGATTCCACTGCCACTTTTCACCAC
GTGACTGGCAAAGACTCATCAACAACAACTGGGGATTCCGACCCAAGAGACTCAACTTCAAGCTCTTTAACATTCAAGTCAAAGAGGT
CACGCAGAATGACGGTACGACGACGATTGCCAATAACCTTACCAGCACGGTTCAGGTGTTTACTGACTCGGAGTACCAGCTCCCGTAC
GTCCTCGGCTCGGCGCATCAAGGATGCCTCCCGCCGTTCCCAGCAGACGTCTTCATGGTGCCACAGTATGGATACCTCACCCTGAACA
ACGGGAGTCAGGCAGTAGGACGCTCTTCATTTTACTGCCTGGAGTACTTTCCTTCTCAGATGCTGCGTACCGGAAACAACTTTACCTT
CAGCTACACTTTTGAGGACGTTCCTTTCCACAGCAGCTACGCTCACAGCCAGAGTCTGGACCGTCTCATGAATCCTCTCATCGACCAG
TACCTGTATTACTTGAGCAGAACAAACACTCCAAGTGGAACCACCACGCAGTCAAGGCTTCAGTTTTCTCAGGCCGGAGCGAGTGACA
TTCGGGACCAGTCTAGGAACTGGCTTCCTGGACCCTGTTACCGCCAGCAGCGAGTATCAAAGACATCTGCGGATAACAACAACAGTGA
ATACTCGTGGACTGGAGCTACCAAGTACCACCTCAATGGCAGAGACTCTCTGGTGAATCCGGGCCCGGCCATGGCAAGCCACAAGGAC
GATGAAGAAAAGTTTTTTCCTCAGAGCGGGGTTCTCATCTTTGGGAAGCAAGGCTCAGAGAAAACAAATGTGGACATTGAAAAGGTCA
TGATTACAGACGAAGAGGAAATCAGGACAACCAATCCCGTGGCTACGGAGCAGTATGGTTCTGTATCTACCAACCTCCAGAGAGGCAA
<u>CACCGGTGTGCCTACTATCGTGATGGTGGACGCCTACAAGCGTTACAAGGGCTTAAGT</u>AGACAAGCAGCTACCGCAGATGTCAACACA
CAAGGCGTTCTTCCAGGCATGGTCTGGCAGGACAGAGATGTGTACCTTCAGGGGCCCATCTGGGCAAAGATTCCACACACGGACGGAC
ATTTTCACCCCTCTCCCCTCATGGGTGGATTCGGACTTAAACACCCTCCTCCACAGATTCTCATCAAGAACACCCCGGTACCTGCGAA
TCCTTCGACCACCTTCAGTGCGGCAAAGTTTGCTTCTTCATCACAGTACTCCACGGGACAGGTCAGCGTGGAGATCGAGTGGGAG
CTGCAGAAGGAAAACAGCAAACGCTGGAATCCCGAAATTCAGTACACTTCCAACTACAACAAGTCTGTTAATGTGGACTTTACTGTGG
ACACTAATGGCGTGTATTCAGAGCCTCGCCCCATTGGCACCAGATACCTGACTCGTAATCTGTA

APPENDIX-continued

SEQUENCES

SEQ ID NO: 8: Part of sequence including the insert (underlined) of AAV2-453-SPYTAG002 (with TG_GLS linkers):
ATGGCTGCCGATGGTTATCTTCCAGATTGGCTCGAGGACACTCTCTCTGAAGGAATAAGACAGTGGTGGAAGCTCAAACCTGGCCCAC
CACCACCAAAGCCCGCAGAGCGGCATAAGGACGACAGCAGGGGTCTTGTGCTTCCTGGGTACAAGTACCTCGGACCCTTCAACGGACT
CGACAAGGGAGAGCCGGTCAACGAGGCAGACGCCGCGGCCCTCGAGCACGACAAAGCCTACGACCGGCAGCTCGACAGCGGAGACAAC
CCGTACCTCAAGTACAACCACGCCGACGCGGAGTTTCAGGAGCGCTTTAAGGAAGATAGCGTCTTTTGGGGGCAACCTCGGACGAGCAG
TCTTCCAGGCGAAAAAGAGGGTTCTTGAACCTCTGGGCCTGGTTGAGGAACCTGTTAAGACGGCTCCGGGAAAAAAGAGGCCGGTAGA
GCACTCTCCTGTGGAGCCAGACTCCTCCTCGGGAACCGGAAAGGCGGGCCAGCAGCCTGCAAGAAAAAGATTGAATTTTGGTCAGACT
GGGAGACGCAGACTCAGTACCTGACCCCCAGCCTCTCGGACAGCCACCAGCAGCCCCTCTGGTCTGGGAACTAATACGATGGCTACAG
GCAGTGGCGCACCAATGGCAGACAATAACGAGGGCGCCGACGGAGTGGGTAATTCCTCGGGAAATTGGCATTGCGATTCCACATGGAT
GGGCGACAGAGTCATCACCACCAGCACCCGAACCTGGGCCCTGCCCACCTACAACAACCACCTCTACAAACAAATTTCCAGCCAATCA
GGAGCCTCGAACGACAATCACTACTTTGGCTACAGCACCCCTTGGGGGTATTTTGACTTCAACAGATTCCACTGCCACTTTTCACCAC
GTGACTGGCAAAGACTCATCAACAACAACTGGGGATTCCGACCCAAGAGACTCAACTTCAAGCTCTTTAACATTCAAGTCAAAGAGGT
CACGCAGAATGACGGTACGACGACGATTGCCAATAACCTTACCAGCACGGTTCAGGTGTTTACTGACTCGGAGTACCAGCTCCCGTAC
GTCCTCGGCTCGGCGCATCAAGGATGCCTCCCGCCGTTCCCAGCAGACGTCTTCATGGTGCCACAGTATGGATACCTCACCCTGAACA
ACGGGAGTCAGGCAGTAGGACGCTCTTCATTTTACTGCCTGGAGTACTTTCCTTCTCAGATGCTGCGTACCGGAAACAACTTTACCTT
CAGCTACACTTTTGAGGACGTTCCTTTCCACAGCAGCTACGCTCACAGCCAGAGTCTGGACCGTCTCATGAATCCTCTCATCGACCAG
TACCTGTATTACTTGAGCAGAACAAACACTCCAAGTGGA<u>ACCGGTGTGCCTACTATCGTGATGGTGGACGCCTACAAGCGTTACAAGG
GCTTAAGT</u>ACCACCACGCAGCTCAAGGCTTCAGTTTTCTCAGGCCGGACGGAGTGACATTCGGGACCAGTCTAGGAACTGGCTTCCTGG
ACCCTGTTACCGCCAGCAGCGAGTATCAAAGACATCTGCGGATAACAACAACAGTGAATACTCGTGGACTGGAGCTACCAAGTACCAC
CTCAATGGCAGAGACTCTCTGGTGAATCCGGGCCCGGCCATGGCAAGCCACAAGGACGATGAAGAAAAGTTTTTTCCTCAGAGCGGGG
TTCTCATCTTTGGGAAGCAAGGCTCAGAGAAAACAAATGTGGACATTGAAAAGGTCATGATTACAGACGAAGAGGAAATCAGGACAAC
CAATCCCGTGGCTACGGAGCAGTATGGTTCTGTATCTACCAACCTCCAGAGAGGCAACAGACAAGCAGCTACCGCAGATGTCAACACA
CAAGGCGTTCTTCCAGGCATGGTCTGGCAGGACAGAGATGTGTACCTTCAGGGGCCCATCTGGGCAAAGATTCCACACACGGACGGAC
ATTTTCACCCCTCTCCCCTCATGGGTGGATTCGGACTTAAACACCCTCCTCCACAGATTCTCATCAAGAACACCCCGGTACCTGCGAA
TCCTTCGACCACCTTCAGTGCGGCAAAGTTTGCTTCCTTCATCACACAGTACTCCACGGGACAGGTCAGCGTGGAGATCGAGTGGGAG
CTGCAGAAGGAAAACAGCAAACGCTGGAATCCCGAAATTCAGTACACTTCCAACTACAACAAGTCTGTTAATGTGGACTTTACTGTGG
ACACTAATGGCGTGTATTCAGAGCCTCGCCCCATTGGCACCAGATACCTGACTCGTAATCTGTA SEQ ID NO: 9: SpyCatcher-VP2 (with SpyCatcher and a long flexible linker underlined):
<u>GCCACCATGGGCTCAGGTGATAGTGCTACCCATATTAAATTCTCAAAACGTGATGAGGACGGCAAAGAGTTAGCTGGTGCAACTATGG
AGTTGCGTGATTCATCTGGTAAAACTATTAGTACATGGATTTCAGATGGACAAGTGAAAGATTTCTACCTGTATCCAGGAAAATATAC
ATTTGTCGAAACCGCAGCACCAGACGGTTATGAGGTAGCAACTGCTATTACCTTTACAGTTAATGAGCAAGGTCAGGTTACTGTAAAT
GGCAAAGCAACTAAAGGTGACGCTCATATTTCAGGTGGTGGCGGTTCAGGCGGAGGTGGCTCTGGCGGTGGCGGATCG</u>GCTCCGGGAA
AAAAGAGGCCGGTAGAGCACTCTCCTGTGGAGCCAGACTCCTCCTCGGGAACCGGAAAGGCGGGCCAGCAGCCTGCAAGAAAAAGATT
GAATTTTGGTCAGACTGGAGACGCAGACTCAGTACCTGACCCCCAGCCTCTCGGACAGCCACCAGCAGCCCCCTCTGGTCTGGGAACT
AATACGATGGCTACAGGCAGTGGCGCACCAATGGCAGACAATAACGAGGGCGCCGACGGAGTGGGTAATTCCTCGGGAAATTGGCATT
GCGATTCCACATGGATGGGCGACAGAGTCATCACCACCAGCACCCGAACCTGGGCCCTGCCCACCTACAACAACCACCTCTACAAACA
AATTTCCAGCCAATCAGGAGCCTCGAACGACAATCACTACTTTGGCTACAGCACCCCTTGGGGGTATTTTGACTTCAACAGATTCCAC
TGCCACTTTTCACCACGTGACTGGCAAAGACTCATCAACAACAACTGGGGATTCCGACCCAAGAGACTCAACTTCAAGCTCTTTAACA
TTCAAGTCAAAGAGGTCACGCAGAATGACGGTACGACGACGATTGCCAATAACCTTACCAGCACGGTTCAGGTGTTTACTGACTCGGA
GTACCAGCTCCCGTACGTCCTCGGCTCGGCGCATCAAGGATGCCTCCCGCCGTTCCCAGCAGACGTCTTCATGGTGCCACAGTATGGA
TACCTCACCCTGAACAACGGGAGTCAGGCAGTAGGACGCTCTTCATTTTACTGCCTGGAGTACTTTCCTTCTCAGATGCTGCGTACCG
CCGGAAACAACTTTACCTTCAGCTACACTTTTGAGGACGTTCCTTTCCACAGCAGCTACGCTCACAGCCAGAGTCTGGACCGTCTCAT
GAATCCTCTCATCGACCAGTACCTGTATTACTTGAGCAGAACAAACACTCCAAGTGGAACCACCACGCAGTCAAGGCTTCAGTTTTCT
CAGGCCGGAGCGAGTGACATTCGGGACCAGTCTAGGAACTGGCTTCCTGGACCCTGTTACCGCCAGCAGCGAGTATCAAAGACATCTG
CGGATAACAACAACAGTGAATACTCGTGGACTGGAGCTACCAAGTACCACCTCAATGGCAGAGACTCTCTGGTGAATCCGGGCCCGGC
CATGGCAAGCCACAAGGACGATGAAGAAAAGTTTTTTCCTCAGAGCGGGGTTCTCATCTTTGGGAAGCAAGGCTCAGAGAAAACAAAT
GTGGACATTGAAAAGGTCATGATTACAGACGAAGAGGAAATCAGGACAACCAATCCCGTGGCTACGGAGCAGTATGGTTCTGTATCTA
CCAACCTCCAGAGAGGCAACAGACAAGCAGCTACCGCAGATGTCAACACACAAGGCGTTCTTCCAGGCATGGTCTGGCAGGACAGAGA
TGTGTACCTTCAGGGGCCCATCTGGGCAAAGATTCCACACACGGACGGACATTTTCACCCCTCTCCCCTCATGGGTGGATTCGGACTT
AAACACCCTCCTCCACAGATTCTCATCAAGAACACCCCGGTACCTGCGAATCCTTCGACCACCTTCAGTGCGGCAAAGTTTGCTTCCT
TCATCACACAGTACTCCACGGGACAGGTCAGCGTGGAGATCGAGTGGGAGCTGCAGAAGGAAAACAGCAAACGCTGGAATCCCGAAAT
TCAGTACACTTCCAACTACAACAAGTCTGTTAATGTGGACTTTACTGTGGACACTAATGGCGTGTATTCAGAGCCTCGCCCCATTGGC
ACCAGATACCTGACTCGTAATCTGTAA SEQ ID NO: 10: Cas9-SpyCatcher002 sequence (SpyCatcher002 underlined):
CATCACCATCACCATCACGAGAACCTCTATTTCCAGGGATCTTCTATGAAAATCGAAGAAGGTAAACTGGTAATCTGGATTAACGGCG
ATAAAGGCTATAACGGTCTCGCTGAAGTCGGTAAGAAATTCGAGAAAGATACCGGAATTAAAGTCACCGTTGAGCATCCGGATAAACT
GGAAGAGAAATTCCCACAGGTTGCGGCAACTGGCGATGGCCCTGACATTATCTTCTGGGCACACGACCGCTTTGGTGGCTACGCTCAA
TCTGGCCTGTTGGCTGAAATCACCCCCGACAAAGCGTTCCAGGACAAGCTGTATCCGTTTACCTGGGATGCCGTACGTTACAACGGCA
AGCTGATTGCTTACCCGATCGCTGTTGAAGCGTTATCGCTGATTTATAACAAAGATCTGCTGCCAAACCCGCCAAAAACCTGGGAAGA
GATCCCGGCGCTGGATAAAGAACTGAAAGCGAAAGGTAAGAGCGCGCTGATGTTCAACCTGCAAGAACCGTACTTCACCTGGCCGCTG
ATTGCTGCTGACGGGGGTTATGCGTTCAAGTATGAAAACGGCAAGTACGACATTAAAGACGTGGGCGTGGATAACGCTGGCGCGAAAG
CGGGTCTGACCTTCCTGGTTGACCTGATTAAAAACAAACACATGAATGCAGACACCGATTACTCCATCGCAGAAGCTGCCTTTAATAA
AGGCGAAACAGCGATGACCATCAACGGCCCGTGGGCATGGTCCAACATCGACACCAGCAAAGTGAATTATGGTGTAACGGTACTGCCG
ACCTTCAAGGGTCAACCATCCAAACGTTCGTTGGCGTGCTGAGCGCAGGTATTAACGCCGCCAGTCCGAACAAAGAGCTGGCAAAAG
AGTTCCTCGAAAACTATCTGCTGACTGATGAAGGTCTGGAAGCGGTTAATAAAGACAAACCGCTGGGTGCCGTAGCGCTGAAGTCTTA
CGAGGAAGAGTTGGCGAAAGATCCACGTATTGCCGCCACTATGGAAAACGCCCAGAAAGGTGAAATCATGCCGAACATCCCGCAGATG
TCCGCTTTCTGGTATGCCGTGCGTACTGCGGTGATCAACGCCGCCAGCGGTCGTCAGACTGTCGATGAAGCCCTGAAAGACGCGCAGA
CTAATTCGAGCTCGAACAACAACAACAATAACAATAACAACAACCTCGGGATCGAGGGAAGGTCTGTACTTCCAATCCAATGCCACCAT
GGATAAGAAATACTCAATAGGCTTAGATATCGGCACAAATAGCGTCGGATGGGCGGTGATCACTGATGAATATAAGGTTCCGTCTAAA
AAGTTCAAGGTTCTGGGAAATACAGACCGCCACAGTATCAAAAAAAATCTTATAGGGGCTCTTTTATTTGACAGTGGAGAGACAGCGG
AAGCGACTCGTCTCAAACGGACAGCTCGTAGAAGGTATACACGTCGGAAGAATCGTATTTGTTATCTACAGGAGATTTTTTCAAATGA
GATGGCGAAAGTAGATGATAGTTTCTTTCATCGACTTGAAGAGTCTTTTTTGGTGGAAGAAGACAAGAAGCATGAACGTCATCCTATT
TTTGGAAATATAGTAGATGAAGTTGCTTATCATGAGAAATATCCAACTATCTATCATCTGCGAAAAAATTGGTAGATTCTACTGATA
AAGCGGATTTGCGCTTAATCTATTTGGCCTTAGCGCATATGATTAAGTTTCGTGGTCATTTTTTGATTGAGGGAGATTTAAATCCTGA
TAATAGTGATGTGGACAAACTATTTATCCAGTTGGTACAAACCTACAATCAATTATTTGAAGAAACCCTATTAACGCAAGTGGAGTA APPENDIX-continued

SEQUENCES

GATGCTAAAGCGATTCTTTCTGCACGATTGAGTAAATCAAGACGATTAGAAAATCTCATTGCTCAGCTCCCCGGTGAGAAGAAAATG
GCTTATTTGGGAATCTCATTGCTTTGTCATTGGGTTTGACCCCTAATTTTAAATCAAATTTTGATTTGGCAGAAGATGCTAAATTACA
GCTTTCAAAAGATACTTACGATGATGATTTAGATAATTTATTGGCGCAAATTGGAGATCAATATGCTGATTTGTTTTTGGCAGCTAAG
AATTTATCAGATGCTATTTTACTTTCAGATATCCTAAGAGTAAATACTGAAATAACTAAGGCTCCCCTATCAGCTTCAATGATTAAAC
GCTACGATGAACATCATCAAGACTTGACTCTTTTAAAAGCTTTAGTTCGACAACAACTTCCAGAAAAGTATAAAGAAATCTTTTTTGA
TCAATCAAAAAACGGATATGCAGGTTATATTGATGGGGGAGCTAGCCAAGAAGAATTTTATAAATTTATCAAACCAATTTTAGAAAAA
ATGGATGGTACTGAGGAATTATTGGTGAAACTAAATCGTGAAGATTTGCTGCGCAAGCAACGGACCTTTGACAACGGCTCTATTCCCC
ATCAAATTCACTTGGGTGAGCTGCATGCTATTTTGAGAAGACAAGAAGACTTTTATCCATTTTTAAAAGACAATCGTGAGAAGATTGA
AAAAATCTTGACTTTTCGAATTCCTTATTATGTTGGTCCATTGGCGCGTGGCAATAGTCGTTTTGCATGGATGACTCGGAAGTCTGAA
GAAACAATTACCCCATGGAATTTTGAAGAAGTTGTCGATAAAGGTGCTTCAGCTCAATCATTTATTGAACGCATGACAAACTTTGATA
AAAATCTTCCAAATGAAAAGTACTACCAAAACATAGTTTGCTTTATGAGTATTTTACGTTTATAACGAATTGACAAAGGTCAAATA
TGTTACTGAAGGAATGCGAAAACCAGCATTTCTTTCAGGTGACAGAAGAAAGCCATTGTTGATTTACTCTTCAAAACAAATCGAAAA
GTAACCGTTAAGCAATTAAAAGAAGATTATTTCAAAAAAATAGAATGTTTTGATAGTGTTGAAATTTCAGGAGTTGAAGATAGATTTA
ATGCTTCATTAGGTACCTACCATGATTTGCTAAAAATTATTAAAGATAAAGATTTTTTGGATAATGAAGAAAATGAAGATATCTTAGA
GGATATTGTTTTAACATTGACCTTATTTGAAGATAGGGAGATGATTGAGGAAAGACTTAAAACATATGCTCACCTCTTTGATGATAAG
GTGATGAAACAGCTTAAACGTCGCCGTTATACTGGTTGGGGACGTTTGTCTCGAAAATTGATTAATGGTATTAGGGATAAGCAATCTG
GCAAAACAATATTAGATTTTTTGAAATCAGATGGTTTTGCCAATCGCAATTTTATGCAGCTGATCCATGATGATAGTTTGACATTTAA
AGAAGACATTCAAAAAGCACAAGTGTCTGGACAAGGCGATAGTTTACATGAACATATTGCAAATTTAGCTGGTAGCCCTGCTATTAAA
AAAGGTATTTTACGACTGTAAAAGTTGTTGATGAATTGGTCAAAGTAATGGGGCGGCATAAGCCAGAAAATATCGTTATTGAAATGG
CACGTGAAAATCAGACAACTCAAAAGGGCCAGAAAAATTCGCGAGAGCGTATGAAACGAATCGAAGAAGGTATCAAAGAATTAGGAAG
TCAGATTCTTAAAGAGCATCCTGTTGAAAATACTCAATTGCAAAATGAAAAGCTCTATCTCTATTATCTCCAAAATGGAAGAGACATG
TATGTGGACCAAGAATTAGATATTAATCGTTTAAGTGATTATGATGTCGATCACATTGTTCCACAAAGTTTCCTTAAAGACGATTCAA
TAGACAATAAGGTCTTAACGCGTTCTGATAAAAATCGTGGTAAATCGGATAACGTTCCAAGTGAAGAAGTAGTCAAAAAGATGAAAAA
CTATTGGAGACAACTTCTAAACGCCAAGTTAATCACTCAACGTAAGTTTGATAATTTAACGAAAGCTGAACGTGGAGGTTTGAGTGAA
CTTGATAAAGCTGGTTTTATCAAACGCCAATTGGTTGAAACTCGCCAAATCACTAAGCATGTGGCACAAATTTTGGATAGTCGCATGA
ATACTAAATACGATGAAAATGATAAACTTATTCGAGAGGTTAAAGTGATTACCTTAAAATCTAAATTAGTTTCTGACTTCCGAAAAGA
TTTCCAATTCTATAAAGTACGTGAGATTAACAATTACCATCATGCCCATGATGCGTATCTAAATGCCGTCGTTGGAACTGCTTTGATT
AAGAAATATCCAAAACTTGAATCGGAGTTTGTCTATGGTGATTATAAAGTTTATGATGTTCGTAAAATGATTGCTAAGTCTGAGCAAG
AAATAGGCAAAGCAACCGCAAAATATTTCTTTTACTCTAATATCATGAACTTCTTCAAAACAGAATTACACTTGCAAATGGAGAGAT
TCGCAAACGCCCTCTAATCGAAACTAATGGGGAAACTGGAGAAATTGTCTGGGATAAAGGGCGAGATTTTGCCACAGTGCGCAAAGTA
TTGGTCCATGCCCCAAGTCAATATTGTCAAGAAAACAGAAGTACAGACAGGCGGATTCTCAAGGAGTCAATTTTACCAAAAAGAAATT
CGGACAAGCTTATTGCTCGTAAAAAAGACTGGGATCCAAAAAAATATGGTGGTTTTGATAGTCCAACGGTAGCTTATTCAGTCCTAGT
GGTTGCTAAGGTGGAAAAGGGAAATCGAAGAAGTTAAAATCCGTTAAAGAGTTACTAGGGATCACAATTATGGAAAGAAGTTCCTTT
GAAAAAAATCCGATTGACTTTTTAGAAGCTAAAGGATATAAGGAAGTTAAAAAAGACTTAATCATTAAACTACCTAAATATAGTCTTT
TTGAGTTAGAAAACGGTCGTAAACGGATGCTGGCTAGTGCCGGAGAATTACAAAAGGAAATGAGCTGGCTCTGCCAAGCAAATATGT
GAATTTTTTATATTTAGCTAGTCATTATGAAAAGTTGAAGGGTAGTCCAGAAGATAACGAACAAAAACAATTGTTTGTGGAGCAGCAT
AAGCATTATTTAGATGAGATTATTGAGCAAATCAGTGAATTTTCTAAGCGTGTTATTTTAGCAGATGCCAATTTAGATAAAGTTCTTA
GTGCATATAACAAACATAGAGACAAACCAATACGTGAACAAGCAGAAAATATTATTCATTTATTTACGTTGACGAATCTTGGAGCTCC
CGCTGCTTTTAAATATTTTGATACAACAATTGATCGTAAACGATATACGTCTACAAAAGAAGTTTTAGATGCCACTCTTATCCATCAA
TCCATCACTGGTCTTTATGAAACACGCATTGATTTGAGTCAGCTAGGAGGTGACGGGTCACCTAAGAAAAAACGAAAAGTTGAGGATC
CTAAAAAGAAACGAAAAGTTGATGGCAGCGGCGGCAGCGGCGGCAGCGGC**GGCGCCATGGTAACCACCTTATCAGGTTTATCAGGTGA
GCAAGGTCCGTCCGGTGATATGACAACTGAAGAAGATAGTGCTACCCATATTAAATTCTCAAAACGTGATGAGGACGGCCGTGAGTTA
GCTGGTGCAACTATGGAGTTGCGTGATTCATCTGGTAAAACTATTAGTACATGGATTTCAGATGGACATGTGAAGGATTTCTACCTGT
ATCCAGGAAAATATACATTTGTCGAAACCGCAGCACCAGAC**GGTTATGAGGTAGCAACTGCTATTACCTTTACAGTTAATGAGCAAGG
TCAGGTTACTGTAAATGGCGAAGCAACTAAAGGTGACGCTCATACTGGATCCAGTGGTAGCTAA

SEQ ID NO: 11: mClover (GFP variant)-SpyCatcher002 sequence (SpyCatcher002
underlined):
CATCACCATCACCATCACGAGAACCTCTATTTCCAGGGAGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGAGGGCGATGCCACCAACGGCAAGCTGACCCTGAAGTT
CATCTGCACCACCGGCAAGCTGCCCGTGCCCTGGCCCACCCTCGTGACCACCTTCGGCTACGGCGTGGCCTGCTTCAGCCGCTACCCC
GACCACATGAAGCAGCACGACTTCTTCAAGTCCGCCATGCCCGAAGGCTACGTCCAGGAGCGCACCATCTCTTTCAAGGACGACGGTA
CCTACAAGACCCGCGCCGAGGTGAAGTTCGAGGGCGACACCCTGGTGAACCGCATCGAGCTGAAGGGCATCGACTTCAAGGAGGACGG
CAACATCCTGGGGCACAAGCTGGAGTACAACTTCAACAGCCACTACGTCTATATCACGGCCGACAAGCAGAAGAACGGCATCAAGGCT
AACTTCAAGATCCGCCACAACGTTGAGGACGGCAGCGTGCAGCTCGCCGACCACTACCAGCAGAACACCCCCATCGGCGACGGCCCCG
TGCTGCTGCCCGACAACCACTACCTGAGCCATCAGTCCAAGCTGAGCAAAGACCCCAACGAGAAGCGCGATCACATGGTCCTGCTGGA
GTTCGTGACCGCCGCCGGGATTACACATGGCATGGACGAGCTGTACAAGGGCAGCGGCGGCAGCGGCGGCAGCGGC**GGCGCCATGGTA
ACCACCTTATCAGGTTTATCAGGTGAGCAAGGTCCGTCCGGTGATATGACAACTGAAGAAGATAGTGCTACCCATATTAAATTCTCAA
AACGTGATGAGGACGGCCGTGAGTTAGCTGGTGCAACTATGGAGTTGCGTGATTCATCTGGTAAAACTATTAGTACATGGATTTCAGA
TGGACATGTGAAGGATTTCTACCTGTATCCAGGAAAATATACATTTGTCGAAACCGCAGCACCAGAC**GGTTATGAGGTAGCAACTGCT
ATTACCTTTACAGTTAATGAGCAAGGTCAGGTTACTGTAAATGGCGAAGCAACTAAAGGTGACGCTCATACTGGATCCAGTGGTAGCT
AA

SEQ ID NO: 12: UAGAGCGUGAGGAAGUUGAU

SEQ ID NO: 13: AGGCCTTCGCAGCATTCTT

SEQ ID NO: 14: GCAGCACCCCATCTGTTTTC

The invention claimed is:

1. A composition comprising a first live adeno-associated virus (AAV) covalently bound to:
   (a) Cas9 via (i) SpyTag and Spy Catcher; (ii) SnoopTag and SnoopCatcher; or (iii) SpyTag002 and SpyCatcher002; and
   (b) a second live AAV via (i) SpyTag and Spy Catcher; (ii) SnoopTag and SnoopCatcher; or (iii) SpyTag002 and SpyCatcher002.

2. The composition of claim 1, wherein the first and second AAV each comprise a different overlapping section of a transgene greater than 4.7 kilobases that encode a protein when assembled via homologous recombination.

3. The composition of claim 1, wherein the first AAV is covalently bound to Cas9 via SpyTag and SpyCatcher.

4. The composition of claim 1, wherein the first AAV is covalently bound to Cas9 via SnoopTag and SnoopCatcher.

5. The composition of claim 1, wherein the first AAV is covalently bound to a third live AAV via (i) SpyTag and Spy Catcher; (ii) SnoopTag and SnoopCatcher; or (iii) SpyTag002 and SpyCatcher002.

6. The composition of claim 1, wherein the first AAV is covalently bound to Cas9 via SpyTag002 and SpyCatcher002.

7. The composition of claim 1, wherein the second live AAV is covalently bound to a second CAS9 via (i) SpyTag and Spy Catcher; (ii) SnoopTag and SnoopCatcher; or (iii) SpyTag002 and SpyCatcher002.

* * * * *